United States Patent [19]
Yang et al.

[11] Patent Number: 6,060,604
[45] Date of Patent: *May 9, 2000

[54] PHARMACEUTICAL COMPOUNDS COMPRISING POLYAMINES SUBSTITUTED WITH ELECTRON-AFFINIC GROUPS

[75] Inventors: Li-Xi Yang; Kurt G. Hofer, both of Tallahassee, Fla.

[73] Assignee: Florida State University, Tallahassee, Fla.

[ * ] Notice: This patent is subject to a terminal disclaimer.

[21] Appl. No.: 08/722,396

[22] Filed: Sep. 30, 1996

Related U.S. Application Data

[63] Continuation-in-part of application No. 08/414,272, Mar. 31, 1995, Pat. No. 5,700,825.

[51] Int. Cl.[7] .................................................. C07D 403/12
[52] U.S. Cl. .......................................................... 548/313.7
[58] Field of Search ........................................ 548/313.7

[56] References Cited

U.S. PATENT DOCUMENTS

| | | | |
|---|---|---|---|
| 2,447,653 | 9/1948 | Johnson | 260/518 |
| 2,653,977 | 9/1953 | Craig et al. | 260/570.5 |
| 3,013,020 | 12/1961 | Fancher | 260/340.5 |
| 4,282,232 | 8/1981 | Agrawal | 424/267 |
| 4,323,689 | 4/1982 | Vogel et al. | 548/336 |
| 4,371,540 | 2/1983 | Lee et al. | 424/273 R |
| 4,456,610 | 6/1984 | Hofheinz et al. | 424/273 R |
| 4,462,992 | 7/1984 | Agrawal et al. | 424/180 |
| 4,665,191 | 5/1987 | Waddill et al. | 548/336 |
| 4,720,586 | 1/1988 | Dixon et al. | 564/341 |
| 4,727,068 | 2/1988 | Abrams et al. | 514/184 |
| 4,797,397 | 1/1989 | Suto et al. | 514/212 |
| 4,803,066 | 2/1989 | Edwards | 424/132 |
| 4,871,759 | 10/1989 | Mercer | 514/398 |
| 4,921,963 | 5/1990 | Skov et al. | 548/101 |
| 4,927,941 | 5/1990 | Kagiya et al. | 548/264.8 |
| 4,945,102 | 7/1990 | Suzuki et al. | 514/398 |
| 4,954,515 | 9/1990 | Suto | 514/398 |
| 4,977,273 | 12/1990 | Kagiya et al. | 548/339 |
| 4,995,898 | 2/1991 | Nasu et al. | 71/90 |
| 5,026,694 | 6/1991 | Skov et al. | 514/184 |
| 5,032,617 | 7/1991 | Lee et al. | 514/617 |
| 5,036,096 | 7/1991 | Suto | 514/398 |
| 5,041,653 | 8/1991 | Lee et al. | 564/74 |
| 5,064,849 | 11/1991 | Suzuki et al. | 514/383 |
| 5,073,566 | 12/1991 | Lifer et al. | 514/381 |
| 5,073,639 | 12/1991 | Suto | 548/339 |
| 5,100,885 | 3/1992 | Abrams et al. | 514/184 |
| 5,175,287 | 12/1992 | Lee et al. | 544/183 |
| 5,183,940 | 2/1993 | Quan et al. | 564/370 |
| 5,196,413 | 3/1993 | Teicher et al. | 514/185 |
| 5,215,738 | 6/1993 | Lee et al. | 424/10 |
| 5,236,944 | 8/1993 | Distelmans et al. | 514/397 |
| 5,270,330 | 12/1993 | Suzuki et al. | 514/398 |
| 5,294,715 | 3/1994 | Papadopoulou-Rosenzweig et al. | 546/106 |
| 5,304,654 | 4/1994 | Kagiya et al. | 548/327.5 |
| 5,342,959 | 8/1994 | Beylin et al. | 548/327.5 |
| 5,371,101 | 12/1994 | Itoh et al. | 514/383 |
| 5,389,661 | 2/1995 | Sircar et al. | 514/381 |
| 5,521,220 | 5/1996 | O'Neill | 514/649 |

FOREIGN PATENT DOCUMENTS

| | | |
|---|---|---|
| 519633 | 12/1955 | Canada . |
| 784711 | 5/1968 | Canada . |
| 0 544 412 A2 | 6/1993 | European Pat. Off. . |
| 2-193979 | 7/1990 | Japan . |
| 6-345728 | 12/1994 | Japan . |
| 2076402 | 12/1981 | United Kingdom . |
| WO 92/03133 | 3/1992 | WIPO . |
| WO 93/13075 | 7/1993 | WIPO . |
| WO 96/0117 | 1/1996 | WIPO . |

OTHER PUBLICATIONS

Aldrich Catalog Handbook of Fine Chemicals, 1994/1995 Ed.

Bruce et al., "Radiation Sensitization of *Micrococcus Radiodurans, Sarcina lutea,* and *Escherichia coli* by p–Hydroxymercuribenzoate," Radiation Research, vol. 24, pp. 473–481, 1965.

Berg et al., "Derivatives of 4–and 5–nitro–2–methylimi–dazol–1–yl–acetaldehyde", European Journal of Med. Chemistry vol. 10, pp. 171–177, 1975.

Mancuso et al., "Oxidation of Long–Chain and Related Alcohols to Carbonyls by Dimethyl Sulfoxide Activated by Oxalyl Chloride[1]", J. Organic Chemistry, vol. 43, pp. 2480–2482, 1978.

Gatenby et al., "Oxygen Distribution in Squamous Cell Carcin–oma Metastases And Its Relationship to Outcome of Radiation Therapy", Int. J. Radiat. Oncol. Biol. Phys., vol. 14, pp. 831–838, 1988.

Carminati et al., "Pathways and Kinetics of Aqueous Decomp–osition and Carbamoylating Activity of New Anticancer Nitroimidazole–Linked 2–chloroethylnitrosoureas," Biochem. Pharmacol., vol. 38, No. 14, pp. 2253–2258, 1989.

(List continued on next page.)

*Primary Examiner*—Johann Richter
*Assistant Examiner*—Joseph Murray
*Attorney, Agent, or Firm*—Senniger, Powers Leavitt & Roedel

[57] ABSTRACT

A compound or a salt thereof comprising a polyamine containing at least 2 electron-affinic groups is provided. In a preferred embodiment, the polyamine compound has the structure:

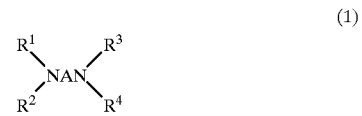

(1)

wherein:

A is a spacer; $R^1$, $R^2$, $R_3$, and $R_4$ are independently hydrogen, hydrocarbon, heterosubstituted hydrocarbon, heteroaryl, heterosubstituted heteroaryl, or an electron-affinic group containing substituent; and the compound contains at least one tertiary amine functionality having three substituents each of which independently contain at least one electron-affinic group or hydrophilic group.

43 Claims, 11 Drawing Sheets

OTHER PUBLICATIONS

Tischler et al., "Taxol: A Novel Radiation Sensitizer," Department of Radiation Oncology, Columbia University, New York, NY, pp. 613–617, 1991.

Holley et al., "Uptake and Cytotoxicity of Novel Nitroimida–zolepolyamine Conjugates in Ehrlich Ascites Tumor Cells," Biochem. Pharmacol., vol. 43, No. 4, pp. 763–769, 1992.

Shenoy et al., "Chemical Radiosensitizers in Cancer Therapy," Cancer Investigation, vol. 10, No. 6, pp. 533–551, 1992.

Tishler et al., "Taxol Sensitizes Human Astrocytoma Cells to Radiation," Cancer Research, vol. 52, pp. 3495–3497, 1992.

DeCross et al., Metronidazole Susceptibility Testing for *Helicobacter pylori*: Comparision of Disk, Broth, and Agar Dilution Methods and Their Clinical Relevance, J. Clin. Microbiology, vol. 31, No. 8, pp. 1971–1974, 1993.

Steren et al., "Taxol Sensitizes Human Ovarian Cancer Cells to Radiation," Gynecologic Oncology, vol. 48, pp. 252–258, 1993.

Steren et al., "Taxol as a Radiation Sensitizer: A Flow Cytometric Study," Gynecologic Oncology, vol. 50, pp. 89–93 1993.

Choy et al., "Investigation of Taxol as a Potential Radiation Sensitizer," Cancer, vol. 71, No. 11, pp. 3774–3778, 1993.

Joschiko et al., "Radiation Enhancement by Taxol in a Squamous Carcinoma of the Hypopharynx (FaDu) in Nude Mice," Proceedings of the American Association for Cancer Research vol. 35, p. 647, 1994.

Milas et al., "Enhancement of Tumor Radioresponse of a Murine Mammary Carcinoma by Paclitaxel[1]," Cancer Research, vol. 54, pp. 3506–3510, 1994.

Hay et al., "Hypoxia–Selective Antitumor Agents. 10. Bis (Nitroimidazoles) and Related Bis(nitroheterocycles): Development of Derivatives with Higher Rates of Metabolic Activation Under Hypoxia and Improved Aqueous Solubility," J. Med. Chem., vol. 38, No. 11, pp. 1928–1941, 1995.

PHARMACEUTICAL COMPOUNDS COMPRISING POLYAMINES SUBSTITUTED WITH ELECTRON-AFFINIC GROUPS

This application is a continuation-in-part of U.S. patent application Ser. No. 08/414,272 filed on Mar. 31, 1995.

BACKGROUND OF THE INVENTION

This invention relates to novel pharmaceutical compounds, and in particular to substituted polyamines containing at least 2 electron-affinic groups; methods of preparing these compounds; and methods of using these compounds in various pharmaceutical applications such as in treating diseases caused by anaerobic and microaerophilic microorganisms and in radiosensitizing hypoxic tumor cells.

In the United States, alone, over a half million patients undergo radiation therapy each year as a part of their battle against cancer. To date, however, radiation therapy has produced only limited success as a cancer treatment. Understandably, therefore, a major effort has been underway for a number of years to develop means to improve the efficacy of such radiotherapy techniques.

It is widely believed that the presence of radioresistant, hypoxic (poorly oxygenated) cells in tumors constitutes a significant factor in causing local failure in conventional cancer radiotherapy. For example, it was reported by Gatenby et al., Int. J. Radiat. Oncol. Biol. Phys. 14: 831–833 (1988), that for head and neck tumors, the hypoxic cell volume is inversely correlated with tumor radiosensitivity. Other reports confirm this conclusion for a variety of types of tumors and suggest that the presence of a concentration of as little as 2–3% hypoxic cells in a tumor may double the radiation dose required for tumor control.

Various solutions have been proposed to overcome the problem of hypoxia, including carrying out radiation treatments in high pressure oxygen chambers and the substitution of "fast neutron" or $\pi$ meson radiation in place of X-rays. However, these techniques are not wholly satisfactory for a number of reasons, including the great expense and difficulty frequently associated with such procedures.

One promising field of investigation for dealing with radioresistant hypoxic tumor cells has been the use of "radiosensitizing" compounds which selectively increase the sensitivity of hypoxic cells to radiation. This specificity to hypoxic cells is also valuable because a significant percentage of solid tumors are characterized by such cells while most normal tissue is not. Thus, treatment with such compounds serves to enhance the impact of radiation on tumor cells while having little effect on the impact of radiation on healthy cell tissue. A number of heterocyclic, electron-affinic compounds, and in particular, those with oxidized nitrogen moieties, have been successfully used for the purpose of radiosensitizing hypoxic tumor cells. Specifically, the discovery that the nitroimidazoles, metronidazole ("metro") and misonidazole ("miso"), sensitize hypoxic cells to radiation provided initial optimism for a breakthrough solution to the problem of tumor hypoxia. Unfortunately, however, both agents have proven to be highly toxic at therapeutic levels. Thus, it is clear that a need exists for more potent radiosensitizing compounds which can be administered at lower doses to reduce toxic side effects.

In addition to being used to radiosensitize hypoxic tumor cells, metronidazole recently has been documented and used as an effective antibiotic against helicobacter pylori ("*H. pylori*") in many countries. *H. pylori*, a fastidious, microaerophilic spiral Gram-negative organism, is well established as a principal cause of gastritis, and as a major contributing factor in the development of peptic gastroduodenal ulcers, gastric carcinoma, and lymphoma. In the United States, *H. pylori* is found in few children, but does colonize the stomach linings of about 20 to 50% of the adults and about 90% of the ulcer patients; the incidence of infection increases with age and is correlated with lower socioeconomic status. In the developing world, the colonization rates generally exceed 80% of the population. Serological evidence shows that 25 to 34% of the United Kingdom population and 52% of the population worldwide are infected. The seriousness of colonization by *H. pylori* in the United States alone is exemplified by the nearly 21,000 deaths per year due to gastric cancer and the 7,000 deaths per year due to gastric and duodenal ulcers. *H. pylori* also has been found in association with dental plaque and saliva, suggesting that the oral environment may be one of the potential pathways for transmission.

Unfortunately, *H. pylori* is a relatively difficult infection to treat. The gastric habitat offers sanctuaries beneath the mucous layer and within the lumen of gastric glands and pits that partially shelter *H. pylori* form the topical or luminal effects of some antibiotics. Gastric acidity inactivates many other antibiotics. Furthermore, *H. pylori* has shown a propensity to rapidly acquire resistance to many classes of antibiotics after exposure to those agents in the form of monotherapy. These include the fluoroquinolones, the macrolides, the nitroimidazoles (including metronidazole), and rifampin.

Therefore, at the present time, no single *H. pylori* eradication regimen is generally accepted by clinicians. The most successful treatment has been achieved using triple therapy wherein metronidazole is administered in conjunction with a bismuth compound and either amoxicillin or tetracycline. Many patients, however, are intolerant to such multiple-antibiotic therapy. In fact, up to 50% of patients have reported some degree of intolerance. This medication intolerance will affect compliance, and it has been shown that compliance is an important factor in the success of triple therapy.

Metronidazole also is disadvantageous due to the existence of metronidazole-resistant *H. pylori* strains. Indeed, the presence of metronidazole-resistant *H. pylori* has been shown to have a considerable impact on the success of triple therapy. One recent report on 40 patients noted a 90.5% bacterial eradication rate for triple therapy (a 2-week course) against metronidazole-susceptible strains, but only a 31.6% bacterial eradication rate against metronidazole-resistant strains (p<0.01) which accounted for 48% of that study's U.K. population. In another study, Decross et al. similarly reported that dual therapy (i.e., bismuth and metronidazole) proved to be highly effective against metronidazole-susceptible strains (81.6% eradication rate) but fared poorly against resistant strains (16.7% eradication rate; p<0.01). Thus, there is a great need to develop novel electron-affinic compounds which are much more effective in killing *H. pylori* than metronidazole, can overcome metronidazole resistance, and have reduced side effects.

In addition to the foregoing uses, metronidazole has been used in various other pharmaceutical applications. For example, metronidazole has been reported to be effective for treating viral infections such as measles, herpes, and viral diverticulitis. It also has been reported to be effective in treating cutaneous inflammation due to dermatosis such as eczema, ulcers, acne, and rosacea. Additionally, it has been reported to be effective in treating eye disorders such as blepharoconjunctivitis and meibomian gland dysfunctions.

Despite these many uses, however, metronidazole is disadvantageous because of its toxicity and various side effects. For example, when it is taken internally, it tends to cause nausea and when it is used in high doses (e.g., when it is used as a radiosensitizer), it tends to cause peripheral neuropathy. In addition, it is disfavored because it is a mutagen. Furthermore, since it is a photosensitizer, it is disfavored for dermatological applications.

Thus, a great need ultimately exists for potent metronidazole substitutes which have less toxicity while being more effective in pharmaceutical applications such as radiosensitizing hypoxic tumor cells and treating internal and dermatological diseases such as infectious diseases caused by anaerobic and microaerophilic microorganisms.

SUMMARY OF THE INVENTION

Among the several objects of the invention, therefore, may be noted the provision of a novel class of pharmaceutical compounds which may be used in place of metronidazole and have less toxicity while being more effective in pharmaceutical applications such as radiosensitizing hypoxic tumor cells and treating internal and dermatological diseases such as infectious diseases caused by anaerobic and microaerophilic microorganisms. Also provided are intermediates and methods for preparation of the pharmaceutical compounds, and techniques for use of such compounds, and pharmaceutical preparations containing them, in treating hypoxic tumor cells and treating internal and dermatological diseases such as infectious diseases caused by anaerobic and microaerophilic microorganisms.

Briefly, therefore, the present invention is directed to a polyamine compound or a salt thereof. The polyamine compound having the structure:

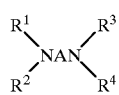
(1)

wherein:

A is a spacer comprising a chain having at least 2 atoms in the chain;

$R^1$ is hydrogen, hydrocarbon, heterosubstituted hydrocarbon, heteroaryl, heterosubstituted heteroaryl, or —L—$(EAG)_a$;

$R^2$ is hydrogen, hydrocarbon, heterosubstituted hydrocarbon, heteroaryl, heterosubstituted heteroaryl, or —L—$(EAG)_b$;

$R^3$ is hydrogen, hydrocarbon, heterosubstituted hydrocarbon, heteroaryl, heterosubstituted heteroaryl, or —L—$(EAG)_c$;

$R^4$ is hydrogen, hydrocarbon, heterosubstituted hydrocarbon, heteroaryl, heterosubstituted heteroaryl, or —L—$(EAG)_d$;

each L is independently a linker comprising a linker chain having at least 1 atom in the chain;

a, b, c, and d are each independently an integer not less than zero, with the sum of a, b, c, and d being no less than 2;

each EAG is independently an electron-affinic group; and the compound contains at least one tertiary amine functionality having three substituents each of which independently contain at least one electron-affinic group or hydrophilic group.

The present invention is further directed to a method for making the polyamine compound. The method comprises reacting an aldehyde having the formula $(EAG)_n$—A'—CHO with a compound having the formula $NH_2$—A—$NH_2$ in the presence of an organic acid and a reducing agent, wherein A' is a linker comprising a bond or a chain of at least 1 atom and n is a natural number.

The present invention is further directed to a method for killing hypoxic tumor cells in a warm-blooded animal. The method comprises (a) administering to the warm-blooded animal the polyamine compound or salt thereof of the present invention in an amount effective to radiosensitize the hypoxic tumor cells, (b) followed by, after a time interval sufficient to enhance radiosensitization of the hypoxic tumor cells, irradiating the hypoxic tumor cells with a dose of radiation effective to kill the hypoxic tumor cells.

The present invention is further directed to a method for treating an internal or dermatological disease in a warm-blooded animal, the method comprising administering to the warm-blooded animal a polyamine compound of the present invention or a salt thereof.

The present invention is further directed to a composition containing an aldehyde of the formula:

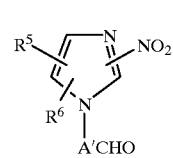
(6)

wherein $R^5$ is hydrogen, lower alkyl or halo;

$R^6$ is hydrogen, lower alkyl, halo or nitro;

A' is a linker comprising a bond or a chain containing at least 1 carbon atom; and the weight ratio of the aldehyde to other compounds in the composition which have as functionality thereof the radical:

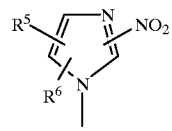

is at least about 1:1. The present invention is further directed to a method for making this aldehyde.

Other objects and features will be in part apparent and in part pointed out hereinafter.

DETAILED DESCRIPTION OF THE PREFERRED EMBODIMENTS

Figure 1:
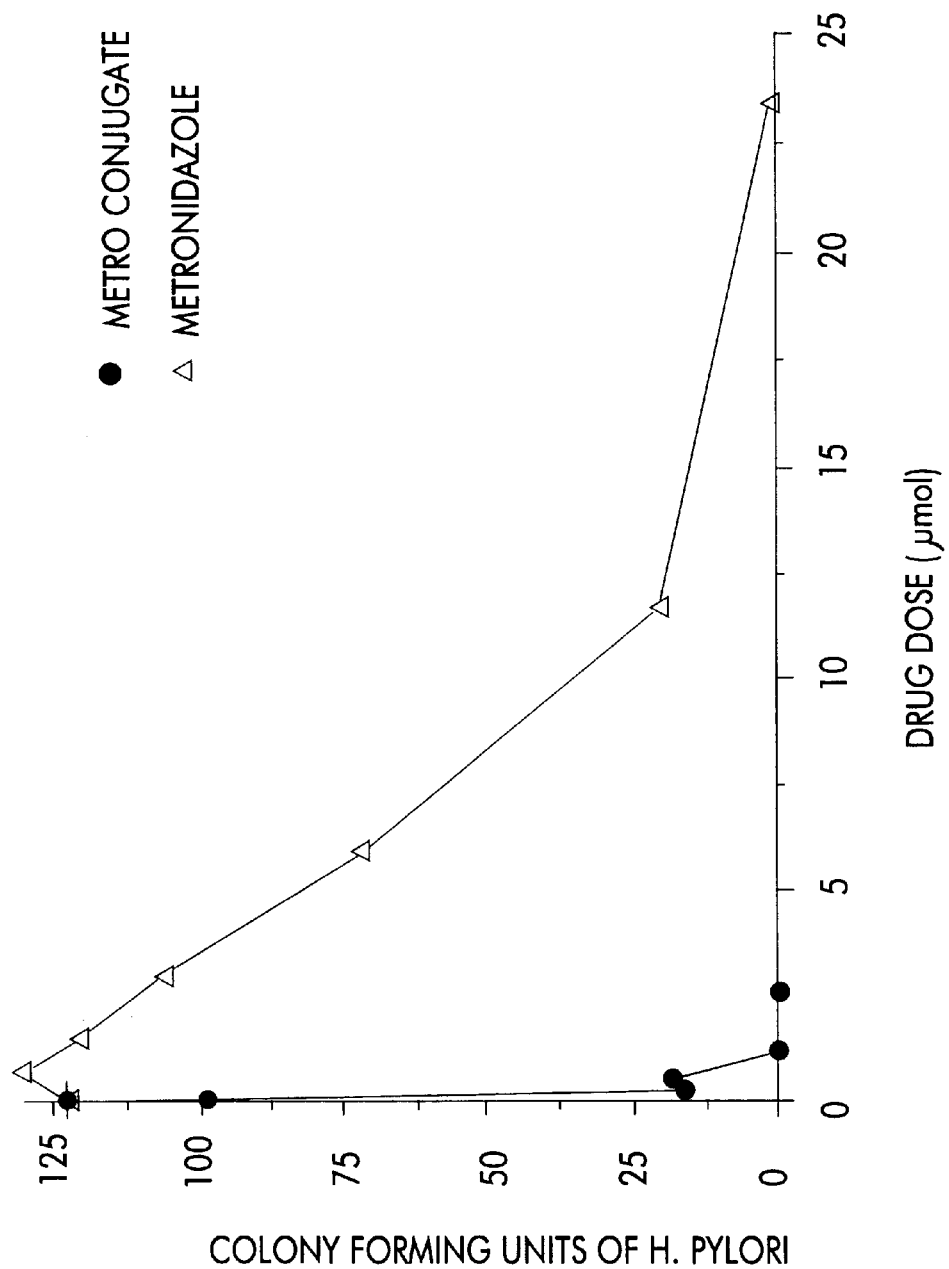
FIG. 1 compares the effects of the 8-carbon DATM (i.e., n=8) metro conjugate and metronidazole on H. Pylori using the agar dilution method.

In accordance with the present invention, multi-functional polyamine derivatives made according to the methods described below have been prepared. Based on the evidence to date, these compounds may be used instead of metronidazole in those applications in which metronidazole is currently being used, and surprisingly, these compounds have been found to be substantially more effective than metronidazole for some of these applications. For example, the compounds of this invention exhibit up to 400 times the radiosensitizing potency of mono-functional radiosensitizing compounds such as metronidazole. Moreover, it has been demonstrated, using the in vitro colony forming assay for evaluating cell survival, that treatment with the polyamines of the present invention under mild hyperthermic conditions renders hypoxic cells more radiosensitive than fully oxic cell populations. As a result, such greatly increased potency permits the administration of much lower dosages of these compounds for the same or even greater radiosensitization of hypoxic tumor cells, allowing for a concomitant reduction in toxic side effects on healthy tissue for any particular dosage level required to effectively radiosensitize the hypoxic tumor cells.

Without being bound by any particular theory, it is hypothesized that the remarkably higher potency exhibited by this class of compounds is due to the synergistic combination of at least two factors. First, the diamine moiety is mildly basic. This is thought to serve as a mechanism for targeting the attached radiosensitizing moieties toward the predominantly acidic hypoxic tumor cells. Further, the diamine is likely to be attracted within such cells to deoxyribonucleic acid (DNA) which is acidic in character, due to its high phosphate content. Second, their greatly enhanced sensitizing potency may also be related to the mechanism of radiation-induced cell death. It is thought that multiple ionizations may be required at or near the DNA for low levels of radiation to cause cell death. Thus, molecules containing multiple radiosensitizing functional groups may be capable of participating in more than one local ionizing event without requiring the close proximity of additional molecules.

In addition to being a novel class of hypoxic tumor-targeted radiosensitizing agents for cancer radiation therapy, the compounds of this invention have been shown to be superior to metronidazole in other applications as well. For example, these compounds have superior chemotherapeutic properties against a variety of anaerobic microorganisms including bacteria and protozoa and, as demonstrated in Example 14, they also have superior chemotherapeutic properties against microaerophilic bacteria such as *H. pylori*. Thus, the compounds of the present invention may be used as effective antimicrobial and antiprotozoal agents in warm-blooded hosts such as humans, cattle, horses, dogs, cats, etc.

This novel class of potent pharmaceutical agents comprises substituted polyamines containing at least 2 electron-affinic groups and the salts thereof. In a preferred embodiment, the agent is a polyamine corresponding to the following structure:

(1)

wherein A, $R^1$, $R^2$, $R^3$, and $R^4$ are as previously defined.

The spacer, A, comprises a chain having at least 2 atoms in the chain (i.e., at least 2 atoms define the backbone of the spacer chain), preferably 2 to about 30 atoms, more preferably at least about 4 to about 20 atoms, and most preferably at least about 6 to about 14 atoms in the chain. In general, compounds with spacer chain lengths shorter than 2 atoms and longer than about 30 atoms tend to be less effective. To illustrate, in the context of radiosensitizing hypoxic tumor cells, radiation is used to cause water molecules in a cell to ionize to —H and —OH radicals. These radicals, in turn, attack the cell's DNA. Strong evidence suggests that cell death occurs when the cell's DNA breaks due to multiple radicals attacking the DNA at locations which are close to each other. Compounds containing electron-affinic groups enhance this process since they interact with the radicals to prevent the radicals from recombining to form water molecules. It is hypothesized that the compounds of the present invention—which contain multiple electron-affinic groups in close proximity with each other—further enhance the effects of radiation therapy by interacting with multiple radicals which are in close proximity with each other. Based on this hypothesis, the spacer in the compound of the present invention preferably is long enough so that the molecule encompasses the DNA double-helix and a sufficient volume of water surrounding the DNA such that the electron-affinic groups can interact with radicals. It also should be sufficiently long so that steric hindrance between the electron-affinic groups is avoided. On the other hand, the spacer preferably is short enough so that multiple electron-affinic groups on the molecule are able to interact with radicals which are close enough to the DNA to be within the radical diffusion limits. Moreover, the spacer preferably is short enough so that the electron-affinic groups interact with multiple radicals which are close enough to each other to enable them to break the cell's DNA by attacking the DNA in locations which are close to each other.

Compounds with spacer chain lengths shorter than 2 atoms and longer than about 30 atoms also tend to be less effective in the context of treating diseases caused by microorganisms. In this context, the electron-affinic groups attack the contents of the cell and create lesions in the cell. It is hypothesized that cell death is more effectively accomplished if these lesions are in close proximity with each other. This is due to the fact that it is more difficult for the cell to repair an area afflicted with multiple lesions relative to an area afflicted with a single lesion. Thus, the length of the spacer chain should be short enough so that the electron-affinic groups attack the cell contents at locations close enough to each other to kill the cell. On the other hand, as stated above, the spacer chain must have sufficient length to avoid steric hindrance between the electron-affinic groups.

The spacer chain atoms, i.e., the atoms defining the backbone of the spacer chain, are preferably selected from the group consisting of C, O, N, S, Si, and P. More preferably, the spacer chain atoms are selected from the group consisting of C, O, and N, with no oxygen atom being directly bonded to another oxygen atom or to a nitrogen atom of the spacer chain. Most preferably, the spacer chain atoms are selected from the group consisting of C and N.

The spacer chain may be linear or non-linear (e.g., it may contain a cycloalkyl or aryl segment), branched or unbranched, and saturated or unsaturated. Additionally, it may contain as substituents one or more P, C, O, N, S, H, Si, or halogen-containing substituents. Exemplary spacer substituents include silyls, ethers, thioethers, esters, thioesters, amides, thioamides, amines, alcohol, alkyl, aryl, carbonyl, sulfonyl, phosphoryl, hydroxyl, carbohydrate, and halogen substituents. Hydrophilic substituents (i.e., substituents containing hydrophilic functional groups such as carbonyl and hydroxyl groups) such as carbohydrates and alcohols are preferred since they tend to impart water solubility to the compound.

Each of $R^1$, $R^2$, $R^3$, and $R^4$, independent of the others, may be selected from the group consisting of hydrogen, hydrocarbon, heterosubstituted hydrocarbon, heteroaryl, heterosubstituted heteroaryl, and —L—$(EAG)_x$ wherein EAG is an electron-affinic group and x is "a" for $R^1$, "b" for $R^2$, "c" for $R^3$, and "d" for $R^4$. In addition, each of a, b, c, and d is zero or a natural number (i.e., an integer not less than zero), with the sum of a, b, c, and d being no less than 2. Also, at least two of $R^1$, $R^2$, $R^3$, and $R^4$ contain an electron-affinic group. In a preferred embodiment, at least one of $R^1$ and $R^2$ contains an electron-affinic group and at least one of $R^3$ and $R^4$ contains an electron-affinic group. More preferably, at least three of $R^1$, $R^2$, $R^3$, and $R^4$ contain at least one electron-affinic group (i.e., at least three of a, b, c and d are greater than zero). Most preferably, $R^1$, $R^2$, $R^3$, and $R^4$ each contain at least one electron-affinic group (i.e., a, b, c, and d are greater than zero).

Each linker, L, independently may be attached to zero, one, or more than one electron-affinic group. Steric hindrance, however, may occur when the linkers are attached to more than three electron-affinic groups; thus, in a more preferred embodiment, the linker, L, is bound to 0 to 3 electron-affinic groups, and a, b, c, and d are each independently an integer of 0–3.

Each L is independently a linker preferably comprising a chain having at least 1 atom. The linker chain atoms, i.e., the atoms defining the backbone of the linker chain, are preferably selected from the group consisting of C, O, N, S, Si, and P. More preferably, the linker chain atoms are selected from the group consisting of C, O, and N, with no oxygen atom being directly bonded to another oxygen atom or to a nitrogen atom of the linker chain. Most preferably, the linker chain atoms are selected from the group consisting of C and N. In general, the considerations discussed above which influence the number of chain atoms in the spacer chain are applicable to the linker chain. Preferably, each linker comprises a chain having about 2 to about 20 chain atoms.

Each EAG is an electron-affinic group or moiety which is selected independent of any other electron-affinic group or moiety in the polyamine. In general, the electron-affinic groups fall into one of the four following categories: (i) carbocyclic or heterocyclic aromatic moieties which possess one or more carbonyl, trifluoromethyl, halogen, nitro, nitroso, N-oxide, sulfonyl, sulfinyl, or phosphoryl groups; (ii) heterocyclic aromatic moieties containing two or more heteroatoms; (iii) metal complexes; and (iv) organo-metallic groups in which the metal is covalently bonded to carbon.

The compound preferably contains at least one tertiary amine. All three substituents of this tertiary amine preferably contain at least one electron-affinic group or hydrophilic functional group. These substituents are advantageous since the hydrophilic functional groups tend to impart water solubility to the compound while the electron-affinic groups tend to increase the effectiveness of the compound in pharmaceutical applications such as when it is used as a radiosensitizer or an antimicrobial agent.

The carbocyclic or heterocyclic aromatic electron-affinic groups contain one to three rings with a total of 5 to 15 ring atoms which are selected from the group consisting of C, N, S, O and P. Preferably, the carbocyclic or heterocyclic aromatic electron-affinic groups contain one to two rings with one ring being presently most preferred. Representative carbocyclic aromatic electron-affinic groups include phenyl and napthyl groups containing one or more nitro, halogen, carbonyl or sulfonyl substituents. Examples of these include quinone groups, semiquinone groups, and nitro-substituted phenyl groups, with the nitro-substituted phenyl groups being preferred. Representative heterocyclic aromatic electron-affinic groups include imidazoles, triazoles, pyridines, benzamides, nicotinamides, benzotriazine oxides, furans, thiophenes, oxazoles and thiozoles possessing one or more carbonyl, trifluoromethyl, halogen, nitro, sulfonyl, sulfinyl, phosphoryl, or oxide groups, and preferably at least one nitro group.

Nitroimidazole and nitrotriazole heterocyclic aromatic electron-affinic groups which may be incorporated into the radiosensitizing agents of the present invention include 2-nitroimidazol-1-yl and 3-nitro-1,2,4-triazol-1-yl and other nitroimidazoles and nitrotriazoles which correspond to the following structures:

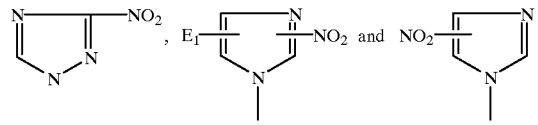

wherein $E_1$ is alkyl or fluoroalkyl. The preparation and use of pharmaceutical compounds incorporating these and other nitroimidazoles and nitrotriazoles is described in Suzuki et al., U.S. Pat. Nos. 4,945,102 and 5,064,849; Kagiza et al., U.S. Pat. Nos. 4,927,941, 4,977,273 and 5,304,654; Suto, U.S. Pat. No. 4,954,515 and 5,036,096; Suto et al., U.S. Pat. No. 4,797,397; Papadopoulou-Rosenzweig et al., U.S. Pat. No. 5,294,715; Beylin et al., U.S. Pat. No. 5,342,959.

Benzamide and nicotinamide heterocyclic aromatic electron-affinic groups which may be incorporated into the pharmaceutical compounds of the present invention include:
5-hydroxynicotinamide;
5-nitronicotinamide;
5-(2,3-dihydroxypropoxy)nicotinamide;
5-aminonicotinamide;
5-(2-methoxyethylamino)nicotinamide;
5-acetamidonicotinamide;
3-hydroxy thiobenzamide;

3-[(2-hydroxyethoxy)acetamido]benzamide;
3-(2,3 dihydroxy-n-propoxy)-4-methoxybenzamide;
3-(2,3 dihydroxy-n-propoxy)-4-methylbenzamide;
4-(2,3 dihydroxy-n-propoxy)-3-methoxybenzamide;
and other benzamides and nicotinamides which correspond to the following structures:

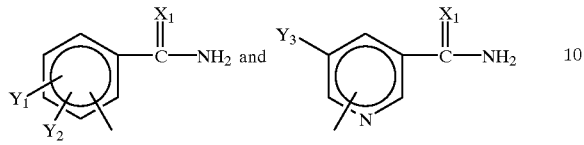

wherein $X^1$ is O or S; $Y_1$ is H, lower alkyl, lower alkoxy, acetoxy, or acetamido; $Y_2$ is —OR, —SR, —NHR, —NO$_2$, —O(CO)R, —NH(CO)R, —O(SO)R, or —O(POR)R; $Y_3$ is H, $Z_1$, —OR, —SR, —NHR, —O(CO)R, —NH(CO)R, —O(SO)R, or —O(POR)R; and R is hydrogen or hydrocarbon which may be optionally substituted and interrupted by an ether (—O—) linkage. The preparation and use of pharmaceutical compounds incorporating these and other benzamides and nicotinamides is described in Lee et al., U.S. Pat. Nos. 5,032,617, 5,041,653 and 5,175,287.

Benzotriazine oxide heterocyclic aromatic electron-affinic groups which may be incorporated into the pharmaceutical compounds of the present invention include:

3-hydroxy-1,2,4-benzotriazine-1,4-dioxide;
3-amino-7-trifluoro-1,2,4-benzotriazine-1-oxide;
3-amino-7-decyl-1,2,4-benzotriazine-1-oxide;
3-amino-7-carbamyl-1,2,4-benzotriazine-1-oxide;
7-acetyl-3-amino-1,2,4-benzotriazine-1-oxide;
7-chloro-3-hydroxy-1,2,4-benzotriazine-1,4-dioxide;
7-nitro-3-amino-1,2,4-benzotriazine-1,4-dioxide; and other benzotriazine oxides corresponding to the structure:

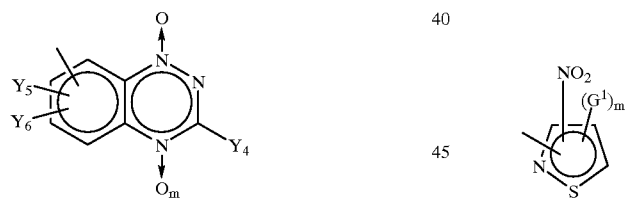

wherein $Y_4$ is H, substituted or unsubstituted lower hydrocarbon, or alkanoyl; m is 0 or 1; and $Y_5$ and $Y_6$ are independently hydrogen, nitro, halogen, morpholino, pyrrolidino, piperidino, substituted or unsubstituted hydrocarbon, —NH$_2$, —NHR', —NR'R'O(CO)R', —NH(CO)R', —O(SO)R', or —O(POR')R' in which R' is substituted or unsubstituted hydrocarbon. The preparation and use of pharmaceutical compounds incorporating these and other benzotriazine oxides is described in Lee et al. U.S. Pat. No. 5,175,287.

The metal complex electron-affinic groups preferably comprise $Pt^{2+}$; $Co^{3+}$, $Fe^{2+}$, $Fe^{3+}$, $Pd^{2+}$, $Cu^{2+}$, $Ti^{4+}$, or $Zr^{4+}$ as the metal and generally fall into two subgroups: (a) metal complexes of the carbocyclic and heterocyclic aromatic electron-affinic groups discussed above, and (b) metal complexes of bidentate ligands comprising nitrogen, carbon or sulfur. In general, metal complexes of bidentate ligands correspond to the formula —$BM^LX_k$ wherein B is a bidentate ligand containing nitrogen, carbon or sulfur, $M^L$ is a metal, X is an anionic ligand such as Cl⁻ or ⁻Oac, and k is 1–4. Exemplary bidentate ligands include:

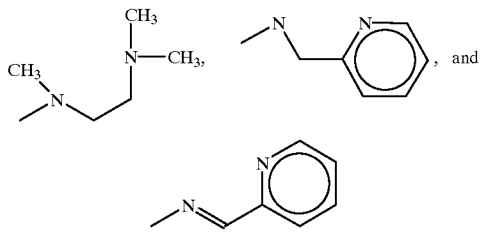

Electron-affinic metal complexes which may be incorporated into the pharmaceutical compounds of the present invention include compounds of the formula:

[PtX$^M_j$(NR$_2$"H)Q] or [PtX$^M_j$(NR$_2$"H)$_2$Q]⁺Y⁻ wherein n is 1 or 2, and wherein when n is 2, $X^M$ is a monovalent biologically acceptable anion, and when j is 1, $X^M$ is a divalent biologically acceptable anion; each R" is independently H or alkyl, or both R"s together are a piperidino or morpholino residue; Q is a functional ligand selected from a mononitro-substituted imidazole, a mononitro-substituted pyrazole, a mononitro-substituted thiazole and a mononitro-substituted isothiazole; and Y⁻ is a physiologically acceptable anion. These heterocycles may optionally be substituted by an alkyl, amino substituted alkyl, hydroxy, alkoxy or amino group. In addition, if the heterocycle is pyrazole or imidazole, a ring nitrogen may be substituted by alkyl or alkoxy or hydroxy substituted alkyl and wherein one or two methylenes of the alkyl may be replaced by oxygen. In a preferred embodiment, Q is one of the following:

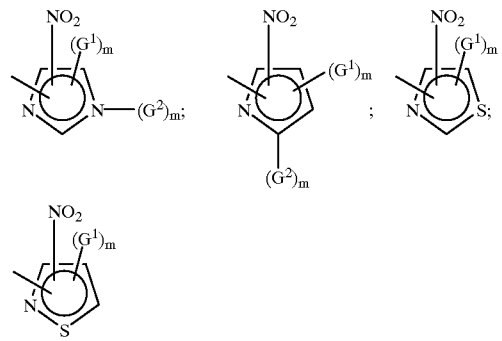

wherein $G^1$ is alkyl optionally containing an amino substituent, —OG$^3$, or —N(G$^3$)$_2$, wherein $G^3$ is H or lower alkyl; $G^2$ is alkyl or 1–8 carbons substituted by one or more —OG$^3$ and wherein one or two methylenes may be replaced by oxygen and each m is independently 0 or 1. The preparation and use of pharmaceutical compounds incorporating these metal complexes is described in Skov et al. U.S. Pat. Nos. 4,921,963 and 5,026,694.

Other electron-affinic metal complexes which may be incorporated into the pharmaceutical compounds of the present invention may be made by reacting an organic or inorganic platinum compound such as an alkali metal tetrahaloplatinate or cis-bis(acetonitrile)dichloro-platinum (II) with rhodamine 123 or other (+)-charged rhodamine or the like, for example, a cyanine dye such as 3,3'-diethylthiadicarbocyanine iodide or other (+)-charged cyanine dyes as described in U.S. Pat. No. 5,196,413.

Other electron-affinic metal complexes which may be incorporated into the pharmaceutical compounds of the present invention include Cu(II) compounds selected from compounds having the formula:

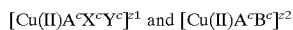

$[Cu(II)A^cX^cY^c]^{z1}$ and $[Cu(II)A^cB^c]^{z2}$ wherein $A^c$ represents a bidentate heteroaromatic ligand containing neutral nitrogen donor atoms; $B^c$ represents a bidentate ligand containing neutral or negatively charged oxygen donor atoms; $X^c$ and $Y^c$ are the same or different neutral or negatively charged monodentate ligands; and $Z^1$ and $Z^2$ represent the charge on the complex. The preparation and use of pharmaceutical compounds incorporating these metal complexes is described in Abrams et al. U.S. Pat. No. 5,100,885.

Other electron-affinic metal complexes which may be incorporated into the pharmaceutical compounds of the present invention include Co(III) or Fe(III) compounds a formula corresponding to one of the following formulas:

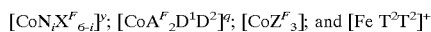

$[CoN_nX^F_{6-i}]^y$; $[CoA^F_2D^1D^2]^q$; $[CoZ^F_3]$; and $[Fe\ T^2T^2]^+$ wherein n has a value of 3 or 4; N is an uncharged nitrogen donor atom that is contained within a ligand; $X^F$ represents an anionic ligand; and y represents the charge on the complex; $A^F$ represents a bidentate or tetradentate negative ligand containing N or O donor atoms; $D^1$ and $D^2$ represent the same or different monodentate ligands; q represents a positive or negative charge on the complex; $Z^F$ represents a chelating mononegative negative ligand; $T^1$ and $T^2$, which may be the same or different, represent mono-negative tridentate ligands. The preparation and use of pharmaceutical compounds incorporating these metal complexes is described in U.S. Pat. No. 4,727,068.

The organometallic electron-affinic groups are aliphatic or aromatic mercury radicals. The preparation and use of pharmaceutical compounds incorporating mercury containing entities is described in Shenoy et al., *Cancer Investigation*, 10(6):533–551 (1992) and Bruce et al., *Radiation Res.*, 24:473–481 (1965).

In one embodiment of the present invention, the substituted polyamine is a diamine having the formula:

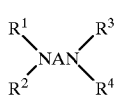

(1)

wherein A comprises a carbon chain having from about 2 to about 10 carbons in the chain, $R^1$, $R^2$, $R^3$, and $R^4$ are H or T, T is

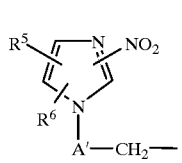

(2)

A' comprises a carbon chain having from about 1 to about 8 carbons in the chain, $R^5$ is H, lower alkyl, or halo, and $R^6$ is H, lower alkyl, halo or nitro. Preferably, at least one of $R^1$ and $R^2$, and at least one of $R^3$ and $R^4$ is T. More preferably, A is alkylene, T is 2-, 4-, or 5-nitroimidazolyl alkyl, particularly 5-nitroimidazolyl alkyl, $R^5$ is ethyl or methyl, particularly 2-methyl, $R^6$ is H, methyl or nitro, particularly H, and A' is ethylene or methylene, particularly methylene.

Preferred diamines having hydrocarbon spacers and linkers correspond to the formula:

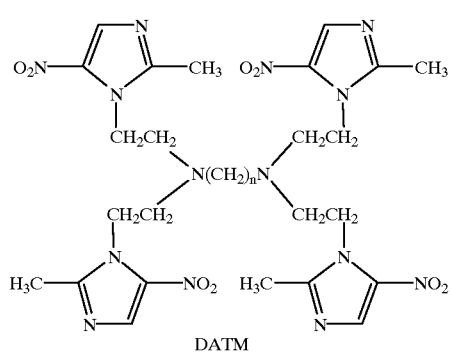

(3)

DATM and

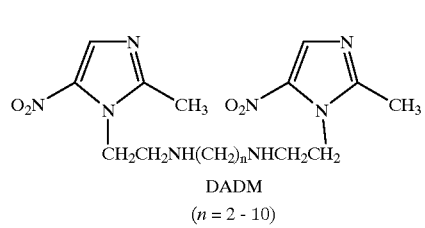

(4)

DADM (n = 2 - 10)

Other exemplary diamines having hydrocarbon spacers and linkers include diaminetetrametronidazoles (DATMs) such as N, N, N', N'-tetra[2'-(2-methyl-5-nitro-1-imidazolyl) ethyl]-1,4-butanediamine; N, N, N', N'-tetra[2'-(2-methyl-5-nitro-1-imidazolyl)ethyl]-1,5-pentanediamine; and N, N, N', N'-tetra[2'-(2-methyl-5-nitro-1-imidazolyl)ethyl]-1,8-octanediamine; and diaminedimetronidazoles (DADMs) such as N, N'-di[2'-(2-methyl-5-nitro-1-imidazolyl)ethyl]-1,4-butanediamine; N, N'-di[2'-(2-methyl-5-nitro-1-imidazolyl)ethyl]-1,5-pentanediamine; and N, N'-di[2'-(2-methyl-5-nitro-1-imidazolyl)ethyl]-1,8-octanediamine.

In a preferred embodiment, the pharmaceutical compounds of the present invention are prepared by linking two or more electron-affinic groups to the nitrogens of primary and secondary amines within a polyamine using an appropriate reaction scheme. Preferably, the electron-affinic groups are linked to the amines using a reductive amination reaction scheme wherein an aldehyde containing one or more electron-affinic groups is treated with a polyamine in the presence of an organic acid (preferably acetic acid) and a reducing agent (preferably $NaBH(OAc)_3$) to obtain the substituted polyamine. For example, the electron-affinic groups may be linked to the terminal nitrogens of an amine-terminated polyamine. In this case, the reagents preferably would be: (1) a polyamine having the general formula $H_2N$—A—$NH_2$, wherein A is a spacer as previously defined; (2) an aldehyde composition having the formula $(EAG)_n$—A'—CHO, wherein each EAG is independently an electron-affinic group, n is a natural number, and A' is a linker comprising a bond or a chain having at least one atom in the chain; (3) an acetic acid; and (4) $NaBH(OAc)_3$. The reductive amination reaction preferably would be:

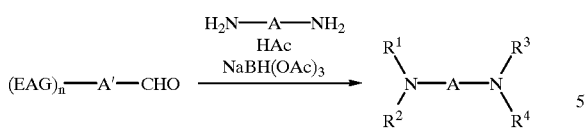

wherein $R^1$, $R^2$, $R^3$, and $R^4$ are each independently H or —$CH_2$—A'—$(EAG)_n$. It should be noted that more than one aldehyde may simultaneously be used in this reaction. Thus, this reaction may be used to produce pharmaceutical compounds wherein $R^1$, $R^2$, $R^3$, and $R^4$ independently contain different electron-affinic substituents.

Representative polyamines which may be used in the reductive amination reaction scheme include 1,3-diaminopropane; 1,4-diaminobutane; 1,5-diaminopentane; 1,8-diaminooctane; 1,7-diaminoheptane; 1,9-diaminononane; 1,10-diaminodecane; 1,12-diaminododecane; DL-2,4-diaminobutyric acid; 1,4-diaminopiperazine; 1,3-diaminoacetone; 1,2-diaminocyclohexane; 1,12-diamino-2-hydroxypropane; 1,8-diaminohydroxypropane; 1,8-diamino-ρ-menthane; 3,3'-diamino-N-methyldipropylamine; 1,2-diamino-2-methylpropane; 2,3-diaminopropionic acid; spermidine (i.e., $H_2N(CH_2)_4NH(CH_2)_3NH_2$); spermine (i.e., $H_2N(CH_2)_3NH(CH_2)_4NH(CH_2)_3NH_2$); N, N'-diethylethylenediamine; N,N'-dimethylethylenediamine; N,N'-dimethyl-1,6-hexanediamine; triethylenetetramine, tetraethylenepentamine, etc. It should be noted that each of the secondary or primary amines which participate in the reductive amination reaction scheme preferably should be bound only to saturated atoms (i.e., the primary amines preferably should be bound to two hydrogens and a saturated atom, and the secondary amines preferably should be bound to a hydrogen and two saturated atoms).

Representative aldehydes which may be used in the amination reductive reaction scheme to prepare the compounds of this invention include trans-2-nitrocinnamaldehyde; 4-nitrocinnamaldehyde; 2-nitrobenzaldehyde; 3-nitrobenzaldehyde; 4-nitrobenzaldehyde; 2-nitrobenzyl-acetaldehyde; 3-nitrobenzyl-acetaldehyde; 4-nitrobenzyl-acetaldehyde; 5-nitro-2-furaldehyde; 5-nitro-2-furyl-acetaldehyde; 5-nitro-2-thiophenecarboxyl-acetaldehyde; 5-nitro-2-thiophenecarboxyl-acetaldehyde; 2-hydroxy-5-nitrobenzyl-acetaldehyde; 6-nitro-4-oxo-4H-1-benzopyran-3-carboxyl-acetaldehyde; 2-methyl-5-nitroimidazol-1-yl-acetaldehyde; 2-nitroimidazol-1-yl-acetaldehyde; 4-nitroimidazol-1-yl-acetaldehyde; 2-hydroxy-5-nitrobenzaldehyde; 3-hydroxy-4-nitrobenzaldehyde; 4-hydroxy-3-nitrobenzaldehyde; 5-hydroxy-2-nitrobenzaldehyde, etc.

To further illustrate the reductive amination scheme, N,N,N',N'-tetra(trans-2-nitrocinnamyl)-1,8-octanediamine may be prepared using the following reaction:

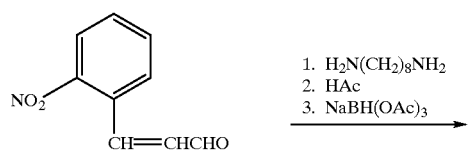

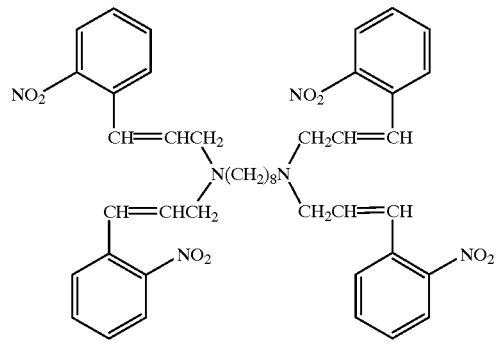

This reaction is further illustrated in Example 7.

As an additional illustration of the reductive amination scheme, this scheme may be used to prepare the preferred polyamines of the formula:

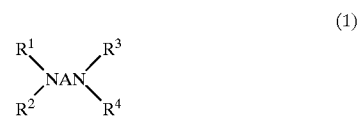

(1)

wherein A comprises a carbon chain having from 2 to about 30 carbons in the chain, $R^1$, $R^2$, $R^3$, and $R^4$ are H or T, T is

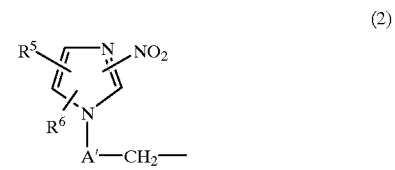

(2)

wherein A' comprises a bond or carbon chain having from one to about 19 carbons in the chain, $R^5$ is H, lower alkyl, or halo, $R^6$ is H, lower alkyl, halo or nitro, and in which at least one of $R^1$ and $R^2$, and at least one of $R^3$ and $R^4$ is T.

First, in order to obtain the aldehyde which is used to prepare this particular compound, nitroimidazoles of formula:

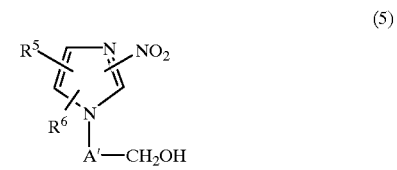

(5)

are oxidized using a mild oxidant, such as dimethyl sulfoxide activated by oxalyl chloride, under conditions favorable to form an aldehyde having the formula

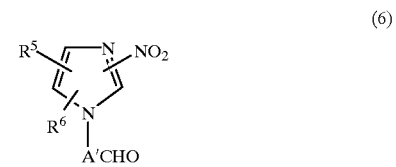

(6)

The aldehyde thus prepared is then treated with a diamine having 2 to about 30 carbons in its main chain in the presence of an organic acid and a reducing agent to obtain the substituted diamine.

Prior to the present invention, the formation of the aldehyde intermediate (formula 6) from metronidazole has been reported to be difficult to achieve. Berg et al. reported a method to produce a crude mixture containing approximately 30% of 2-methyl-5-nitroimidazol-1-yl-acetaldehyde in a complex with the unchanged alcohol in *European Journal of Med. Chemistry* 10: 171–177 (1975). Their attempts to isolate pure aldehyde from this mixture, however, resulted in its decomposition. Oxidation of metronidazole using chromic acid, chromic acid-pyridine, tert-butyl chromate, silver carbonate on celite and 1-chlorobenztriazole only produced the corresponding acid. When the oxidation by chromic acid was performed at room temperature, a mixture containing about 7% of 2-methyl-5-nitroimidazol-1-yl-acetaldehyde was obtained. Berg and Sharp used potassium dichromate-acetic acid to oxidize metronidazole, but were only able to obtain a mixture containing up to 30% aldehyde which, as mentioned, could not be isolated without decomposing.

Conversion of metronidazole (1-(2-hydroxyethyl)-2-methyl-5-nitroimidazole) to the aldehyde was also difficult to achieve because nitroimidazoles do not readily dissolve in solvent solutions in which the oxidation may be carried out. However, applicants have discovered that metronidazole can be dissolved using dimethyl sulfoxide activated by oxalyl chloride. The reaction product is a mixture containing the metronidazole starting material, the desired aldehyde and other nitroimidazole by-products. Advantageously, the reaction product contains greater than 50% by weight of the desired nitroimidazolylalkyl aldehydes, and more preferably contains at least about 85% by weight, typically greater than 90% by weight of the desired nitroimidazolylalkyl aldehydes. From these compositions, the desired nitroimidazolylalkyl aldehydes may be isolated in substantially pure form.

The process for producing the aldehyde is carried out using a modified Swern oxidation reaction (see Huang and Swern, J. Organic Chemistry 43: 2480–2482, 1978), at a reaction mixture temperature of between about −45° C. and about −65° C., preferably at about −50° C. The dimethyl sulfoxide is activated using oxalyl chloride reacts with alcohols to form alkoxysulfonium salts. The alkoxysulfonium salts are readily converted to carbonyl compounds upon addition of triethylamine or the like to form the corresponding aldehyde. Applicants have further discovered that the results are enhanced substantially if the reaction mixture is heated (e.g., by removing dry ice and acetone used as a cold source) for no more than about 10 minutes at the conclusion of the oxidation step, prior to commencing the reductive amination of the aldehyde described below.

The disclosed oxidation process step used, e.g., to form 2-methyl-5-nitroimidazol-1-yl-acetaldehyde, which has the following structural formula:

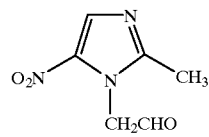

(7)

is illustrated by the following reaction scheme:

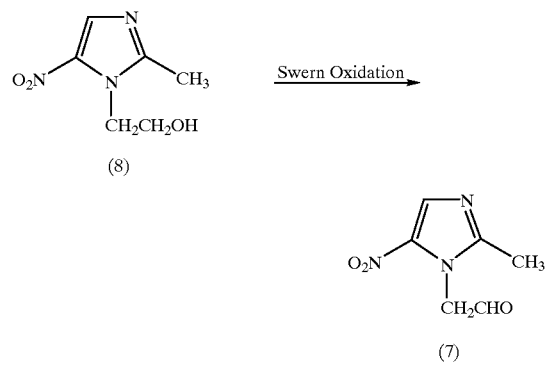

$CH_2Cl_2$ is added to oxalyl chloride under nitrogen gas. The solution is cooled to −50° C. and $Me_2SO$ is then added dropwise to the stirred solution. Metronidazole [1-(2-hydroxyethyl)-2-methyl-5-nitroimidazole] dissolved in $Me_2SO$ is added. After additional stirring, triethylamine is added, and the reaction mixture is stirred again and allowed to warm to room temperature. The resultant mixture is diluted, washed, extracted, filtered and dried to obtain the isolated and substantially purified aldehyde.

Once the isolated aldehyde is prepared, the preferred di- and tetra-nitroimidazolylalkyl polyamines are synthesized by the reductive amination reaction scheme. The aldehyde is reacted with diamines having about 2 to 30 carbons in their main chain in the presence of an organic acid and a mild reducing agent, via reductive amination as shown in the following:

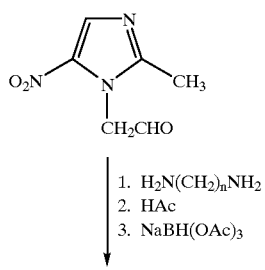

1. $H_2N(CH_2)_nNH_2$
2. HAc
3. $NaBH(OAc)_3$

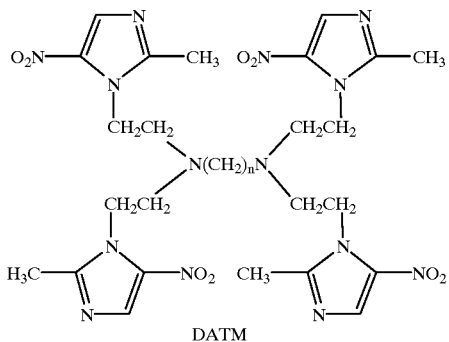

DATM (n = 2 to about 30)

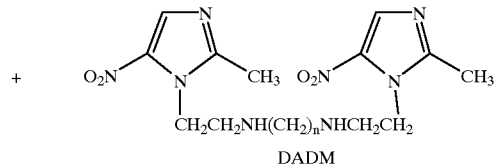

DADM

Sodium triacetoxyborohydride [NaBH(Oac)₃] is advantageously used as a mild and selective reducing agent in the reduction step. The reaction mixture in the reduction step is acidified using an organic acid, preferably acetic acid. If the desired product is DADM, the reaction proceeds most favorably when the relative amounts of the reactants (i.e., the molar ratio of aldehyde to diamine) is about 2.1:1. If, on the other hand, the desired product is DATM, the reaction proceeds most favorably when the relative amounts of reactants (i.e., the molar ratio of aldehyde to diamine) is about 4.1 to 1. In either case, the DADM and DATM may be separated using liquid/liquid extraction. This is further illustrated in Examples 2, 3, and 4.

The reductive amination reaction scheme is not limited to diamines. Indeed, primary or secondary amines in the spacer or in one or more of the linker chains may participate in the reductive amination scheme. This is particularly beneficial since it allows for more than four electron-affinic groups to be present in the compound. To illustrate how additional electron-affinic groups may be attached to polyamines having three or more amines, N-[2'-(2-methyl-5-nitro-1-imidazolyl)ethyl]-N-{3-N'',N''-di[2'-(2-methyl-5-nitro-1-imidazolyl)ethyl]-aminopropyl}-N',N'-di[2'-(2-methyl-5-nitro-1-imidazolyl]-1,4-butanediamine may be prepared using the following reaction scheme:

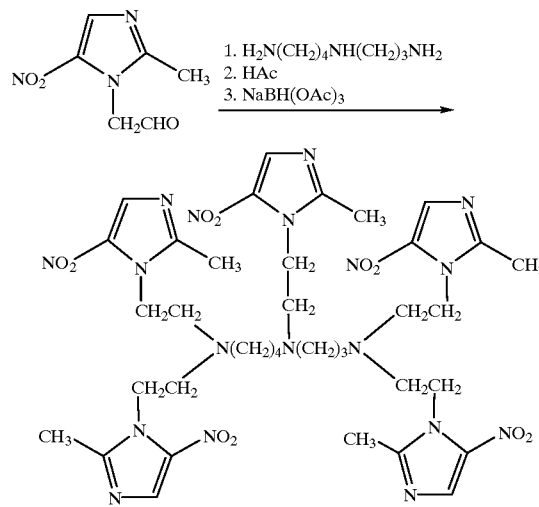

Example 9 further illustrates this preparation procedure.

The reductive amination reaction scheme has the advantage of being an efficient and convenient "one vessel" reaction that permits simultaneous preparation of both di- and tetra-nitroimidazolylalkyl diamines.

Because reaction symmetry favors the addition of either two or four functional groups during reductive amination, the attachment of an appropriate blocking group to one of the terminal amines is required in order to form a substituted diamine containing three radiosensitizing functional groups. To illustrate, a compound having the formula $CH_3-CH_2-NR-(CH_2)_n-N(R)_2$ (wherein n is an integer no less than 2 and R is 1-(ethyl)-2-methyl-5-nitroimidazole) may be prepared using the following reaction scheme:

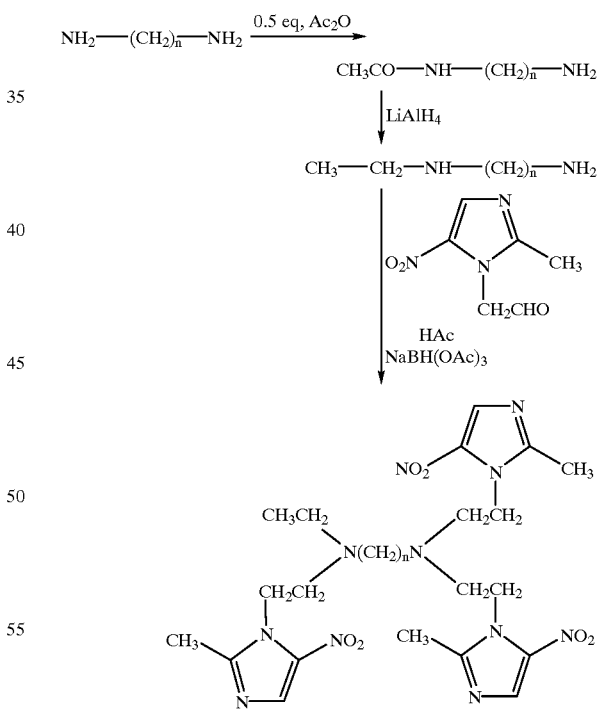

This reaction is further illustrated in Example 8.

In another preferred embodiment, electron-affinity is imparted to the pharmaceutical compounds of the present invention by at least one metal complex in which two amines are bound to a single metal atom through coordinate covalent bonds. The complex may comprise two amines which are on separate molecules, for example:

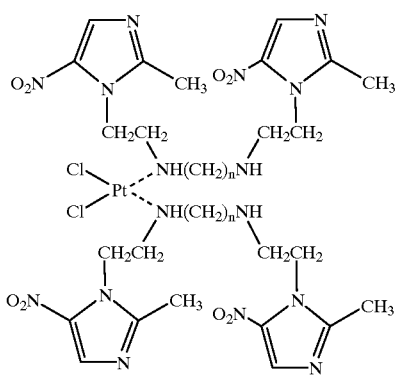

(17)

Alternatively, the complex may comprise two amines which are in the same molecule. In this instance, the nitrogens of the two amines preferably are separated by 2 or 3 carbons. To illustrate, the compound may have the formula:

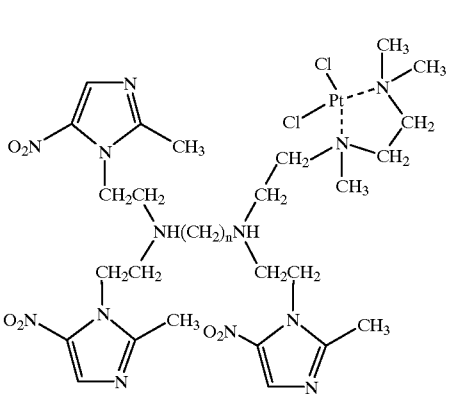

(18)

($n > 1$)

As a further illustration, the compound may have the formula:

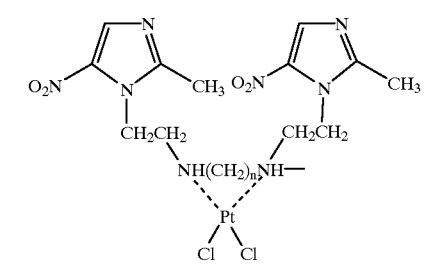

(19)

($n$ is 2 or 3)

Preparation of such compounds is illustrated in Examples 10, 11, and 12.

In one embodiment of this invention, the pharmaceutical compounds contain at least one hydrophilic substituent. These hydrophilic substituents comprise one or more hydrophilic functional groups The term "hydrophilic functional group" as used herein means any functional group which tends to impart water solubility to the compound with which it is associated. In other words, a "hydrophilic functional group" makes the compound to which it is attached more water soluble relative to the corresponding alkyl or hydrocarbon substituted compound. Exemplary hydrophilic functional groups include —$SO_3H$, —OH, —$NH_2$, —COOH, —COOR, and —OR groups (R being hydrocarbon, heterosubstituted hydrocarbon, heteroaryl, or heterosubstituted heteroaryl), with the —OH, —COOH, —$SO_3H$, and —$NH_2$ groups being preferred. Thus, for example, the polyamine of the present invention may be substituted with a heterosubstituted hydrocarbon such as a sulfonic acid, alcohol, carbohydrate, amine, carboxylic acid, ester or ether.

An addition-elimination/reduction reaction scheme may be used to attached at least one hydrophilic substituent to the compound of this invention by linking the hydrophilic substituent to a nitrogen of a primary or secondary amine in the compound. This reaction scheme employs: (1) a compound containing at least one primary or secondary amine; (2) a compound containing a carboxylic acid functional group and a separate hydrophilic functional group; and (3) $Ac_2O$. The carboxylic acid compound reacts (via an addition-elimination reaction) with the compound containing the primary or secondary amine to form an amide. Acetic anhydride then is added to reduce the amide to the corresponding amine. Thus, for example, before adding any electron-affinic groups to an amine-terminated polyamine, a hydrophilic substituent (—$CH_2$—Y, wherein Y is a radical containing at least one hydrophilic functional group) may be attached to one of the terminal amines via the following reaction:

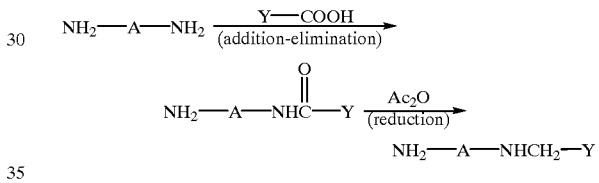

It should be noted that the addition-elimination/reduction reaction scheme also may be used to attach hydrophilic groups to polyamines other than those which are amine-terminated—the polyamine preferably need only have a primary or secondary amine. It also should be noted that this reaction scheme may be used to attach hydrophilic groups to primary and secondary amines on a polyamine before or after electron-affinic groups have been attached.

To add a hydrophilic substituent to a polyamine, the molar ratio of the carboxylic acid compound to the polyamine preferably is about 1:1. Carboxylic acid compounds which may be used preferably have a molecular weight of no more than 400. Suitable compounds include 8-aminocaprylic acid, sulfosuccinic acid, citric acid, gluconic acid, aspartic acid, glutamic acid 5-methyl ester, methoxyacetic acid, glutamic acid, ρ-L-glutamyl-L-glutamic acid, asparagine, threonine, serine, lactic acid, ribose, ascorbic acid, glutaric acid, glucuronic acid, lactobionic acid, glycolic acid, etc. Of these compounds, the most preferred are citric acid, lactic acid, ribose, ascorbic acid, lactobionic acid, and glucuronic acid.

The compounds of the present invention may be converted to their corresponding salts to assist in their formulation into water soluble pharmaceutical compositions. Examples of pharmaceutically acceptable salts include the salts formed by reaction of the substituted polyamines of the invention with gluconic acid, HCl, $H_3PO_4$, maleic acid, oxalic acid, acetic acid, sulfonic acid, sulfuric acid, nicotinic acid, glucuronic acid, and lactobionic acid.

The procedure for converting the compounds of the present invention into the corresponding salts is straightforward. For example, the compound may be dissolved in methanol and then treated with an HCl/ethanol solution wherein the moles of acid used preferably is about equal to the moles of amine groups present in the compound. This solution is then cooled to facilitate precipitation of the salt. Ether also may be added to facilitate precipitation. The precipitate is then recovered by suction filtration, and recrystallized with methanol and ether Methods for obtaining salts are further illustrated in Examples 5 and 6.

The polyamine derivatives of the present invention, particularly in the form of the salts just described, can be combined with various excipient vehicles and/or adjuvants well known in this art which serve as pharmaceutically acceptable carriers to permit drug administration in the form of, e.g., injections, suspensions, emulsions; tablets, capsules, and ointments. For warm-blooded animals, and in particular, for humans, administration can be oral, parenteral, subcutaneous, intravenous, intramuscular and/or intraperitoneal, and for dermatological diseases, topical also. The specific dosage administered will be dependent upon such factors as the general health and physical condition of the patient as well as his age and weight, the stage of the patient's disease condition, and the existence of any concurrent treatments.

To destroy hypoxic tumor cells, the pharmaceutical compounds of this invention may be administered by any acceptable means which results in the radiosensitization of hypoxic tumor cells. The compounds preferably are administered in an amount effective to radiosensitize the hypoxic tumor cells (preferably in the range of 1 to 100 mg per kg of body weight for humans). In this context, the electron-affinic group provides a redox potential or one-electron reduction potential (E-1) sufficiently high to react with radiation-induced water radicals, resulting in radiosensitization in hypoxic tumor cells. After administration of the radiosensitizing composition to the hypoxic tumor cells and the passage of a time interval sufficient to enhance radiosensitization of the hypoxic tumor cells, the hypoxic tumor cells are irradiated with a dose of radiation effective to destroy the hypoxic tumor cells. Generally, the patient will receive a total radiation dosage of about 60 to 76 Gy over seven to eight weeks, each individual radiation dose to be given within approximately 1 to 4 hrs after administration of the radiosensitizer. Such sequences of radiosensitization treatments and irradiation are repeated as needed to abate and, optimally, reduce or eliminate, the spread of the malignancy.

The radiosensitization provided by the radiosensitizing polyamines of the present invention is significantly enhanced when combined with concurrent heat treatment of the hypoxic tumor cells. Such heat treatment may be carried out, e.g., by immersion in a warm water bath preheated to a temperature of from about 37° C. to about 41° C., or by local heating of tumors with microwave applicators.

To treat other internal diseases (such as internal infectious diseases caused by anaerobic microorganisms, microaerophilic microorganisms, etc.), the pharmaceutical compounds of this invention preferably are administered in an amount from about 1 and to about 50 mg per kg of body weight for humans and other animals This treatment preferably should be repeated 2 times per day for at least 3 days. More preferably, this treatment should be repeated 2 times per day for at least one week or until the subject is cured.

To treat dermatological diseases (such as infectious diseases caused by anaerobic microorganisms, microaerophilic microorganisms, etc.), the pharmaceutical compounds of this invention typically are administered by applying an oil-based or water-based lotion, ointment, or cream to the infected area The concentration of the lotion, ointment, or cream preferably is from about 1 to about 50 mg per g (or ml) of lotion, ointment, or cream. This concentration will vary according to the type and extent of the disease The pH of the lotion, ointment, or cream preferably is about 7. This treatment preferably should be repeated 2 times per day until the disease is gone. For severe infections, the pharmaceutical compounds also may be administered orally, subcutaneously, intravenously, intramuscularly, and/or parenterally at concentrations of from about 1 and to about 50 mg per kg of body weight. This treatment preferably should be repeated two times per day for at least 3 days, and more preferably for at least one week or until the subject is cured.

Definitions

Unless otherwise stated, the following definitions should be used:

The hydrocarbon moieties described herein are preferably organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like. They may be substituted with aliphatic or cyclic hydrocarbon radicals or hetero-substituted.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbon radicals or hetero-substituted.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbon radicals or hetero-substituted.

The aryl moieties described herein preferably contain from 6 to 20 carbon atoms and include phenyl. They may be hydrocarbon or heterosubstituted. Phenyl is the more preferred aryl.

The heteroaryl moieties described herein are preferably heterocyclic compounds or radicals which are analogous to aromatic compounds or radicals and which contain a total of 5 to 20 atoms, usually 5 or 6 ring atoms, and at least one atom other than carbon, such as furyl, thienyl, pyridyl and the like. The heteroaryl moieties may be substituted with hydrocarbon, heterosubstituted hydrocarbon or hetero-atom containing substituents with the hetero-atoms being selected from the group consisting of nitrogen, oxygen, silicon, phosphorous, boron, sulfur, and halogens. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The heterosubstituted hydrocarbon moieties described herein are preferably hydrocarbon moieties which are substituted with at least one atom other than carbon, including moieties in which a carbon chain atom is substituted with a hetero atom such as nitrogen, oxygen, silicon, phosphorous, boron, sulfur, or a halogen atom. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The acyl moieties described herein preferably contain hydrocarbon, substituted hydrocarbon or heteroaryl moieties.

To further illustrate and explain the invention, several examples are presented below.

EXAMPLE 1

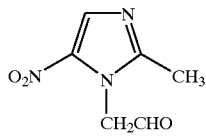

(7)

Preparation of 2-methyl-5-nitroimidazol-1-yl-acetaldehyde

To 160 ml of $CH_2Cl_2$ was added dropwise 2 ml (22 mmol) of oxalyl chloride under nitrogen gas. The solution was cooled to −50° C. and 17 ml (240 mmol) of $Me_2SO$ was added dropwise to the stirred solution. About 20 min later, 3.42 g (20 mmol) of metronidazole [1-(2-hydroxyethyl)-2-methyl-5-nitroimidazole] dissolved in 15 ml of $Me_2SO$ was added After 20 min of additional stirring, 33 ml (240 mmol) of triethylamine was added. The reaction mixture was stirred for another 10 min and then allowed to warm to room temperature. The mixture was diluted with 400 ml of ethyl acetate and washed 4 times with water, first with 100 ml and then 3 times with 50 ml. The 250 ml water volume was extracted 3 times with 250 ml of ethyl acetate and the ethyl acetate was added to the $CH_2Cl_2$. The mixture was washed with 100 ml of saturated NaCl solution, dried over anhydrous $MgSO_4$, filtered, and concentrated to dryness in a rotary evaporator. The resulting crude residue was purified by flash silica gel chromatography to give the pure desired aldehyde (2-methyl-5-nitroimidazol-1-yl-acetaldehyde).

The chemical structure of the resulting pure aldehyde was evaluated by $^1H$ NMR (CDCl, 300 Mhz) δ9.76 (s, 1H, CHO), 7.99 (s, 1H, imidazole H), 5.21 (s, 2H, $CH_2CHO$), 2.41 (s, 3H, $CH_3$)

EXAMPLE 2

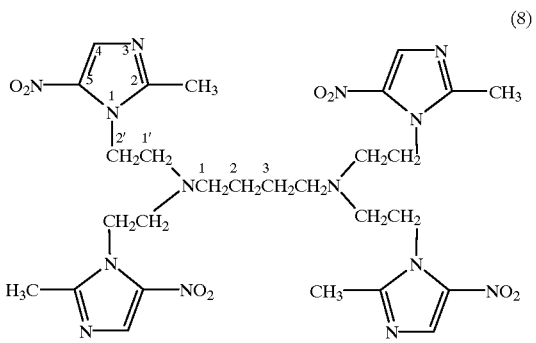

(8)

Preparation of N, N, N', N'-tetra [2'-(2-methyl-5-nitro-1-imidazolyl)ethyl]-1,4-butanediamine The 2-methyl-5-nitroimidazol-1-yl-acetaldehyde (3.0 g, 17.6 mmol) synthesized by the procedure described in Example 1 was dissolved in 80 ml of 1, 2-dichloroethane, 0.44 ml of butanediamine (4.4 mmol) was added, the reaction mixture was stirred for 30 min and then acidified with 1 ml of acetic acid (17.6 mmol). Then 4.48 g of sodium triacetoborohydride (21.12 mmol) was added as a reducing agent and the solution was stirred for 48 h at room temperature. During the entire procedure the reaction vessel was gassed with nitrogen. The resulting mixture was diluted with 60 ml of ethyl acetate, and the mixture solution was washed with 85 ml of saturated aqueous $NaHCO_3$ and 30 ml of water. The aqueous solution was combined for further extraction of compound (5). The organic layer was dried over anhydrous $MgSO_4$, and the solvent was evaporated to leave residual oil which solidified at 4° C. for 2 days. The obtained solid was recrystallized from ethyl acetate/hexane to give N, N, N', N'-tetra[2'-(2-methyl-5-nitro-1-imidazolyl) ethyl]-1,4-butanediamine (m.p. 194°–196° C.).

The chemical structure of the target compound was evaluated by $^1H$ NMR (CDCl$_3$, 300 Mhz) δ7.93(s, 4H, imidazole H4); 4.28 (t, J=6.6 Hz, 8H, H2'); 2.81 (t, J=6.6 Hz, 8H, H1'); 2.55–2.52 (m, 4H, H1, H4); 2.52 (s, 12H, imidazole Me2); 1.25–1.23 (m, 4H, H2, H3).

(9)

$O_2N$ ... $CH_3$   $O_2N$ ... $CH_3$
       |2' 1'  1  2  3  4
       $CH_2CH_2NHCH_2CH_2CH_2CH_2NHCH_2CH_2$

Preparation of N, N'-di[2-(2-methyl-5-nitro-1-imidazolyl)-1, 4-butanediamine

The above combined aqueous solution was reextracted 3 times with 250 ml of ethyl acetate and 3 times with 500 ml of methylene chloride. The methylene chloride solution was washed with 40 ml of water, dried over MgSO4, and evaporated under reduced pressure. The residual oil was cooled at 4° C. for crystallization. The resulting solid was recrystallized from ethyl acetate/hexane to give N, N'di[2'-(2-methyl-5-nitro-1-imidazolyl)-1,4-butanediamine.

The chemical structure analysis was performed by $^1H$ NMR (CDCl$_3$, 300 Mhz) δ7.93(s, 2H, imidazole H4); 4.38 (t, J=6.6 H$^z$, 4H, H1'); 2.57–2.53 (m, 4H, H1, H4); 2.50(s, 6H, imidazole Me2); 1.75 (br, s, 2H, NH, N'H); 1.40–1.39 (m, 4H, H2, H3)

EXAMPLE 3

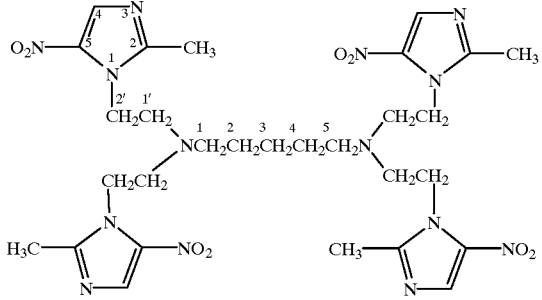

Preparation of N, N, N', N'-tetra[2'-(2-methyl-5-nitro-1-imidazolyl) ethyl]-1, 5-pentanediamine The 2-methyl-5-nitroimidazol-1-yl-acetaldehyde (3.6 g, 19.5 mmol) synthesized by the procedure described in Example 1 was dissolved in 80 ml of 1, 2-dichloroethane, 0.57 ml of pentanediamine (4.88 mmol) was added, the reaction mixture was stirred for 30 min and then acidified with 1.11 ml of acetic acid (19.5 mmol). Then 4.96 g of sodium triacetoxyborohydride (23.4 mmol) was added as a reducing agent and the solution was stirred for 48 h at room temperature. During the entire procedure the reaction vessel was gassed with nitrogen. The resulting mixture was diluted with 60 ml of ethyl acetate, and the mixture solution was washed with 85 ml of saturated aqueous $NaHCO_3$ and 30 ml of water. The aqueous solution was combined for further extraction of target compound (11). The organic layer was dried over anhydrous $MgSO_4$, and the solvent was evaporated to leave residual oil which solidified at 4° C. for 2 days. The final solid was recrystallized from ethyl acetate/hexane to give N, N, N', N'-tetra[2'(2-methyl-5-nitro-1-imidazolyl) ethyl]-1, 4-pentanediamine (m.p. 150°–151° C.).

The chemical structure analysis was performed by $^1H$ NMR ($CDCl_3$, 300 MHz) δ7.93 (s, 4H, imidazole H4); 4.24 (t, J=7.2 $H^z$, 8H, H2'); 2.78 (t, J=7.2 $H^z$, 8H, H1') 2.51–2.49 (m, 4H, H1, H5); 2.49(s, 12H, imidazole Me2); 1.26–1.20 (m, 4H, H2, H4); 1.1 (m, 2H, H3). Also the number of carbon atoms was evaluated by $^{13}C$ NMR ($CDCl_3$, 75 MHz) δ150.526 (imidazole C5); 138.992 (imidazole C2); 133.134 (imidazole C4); 54.599 (C2'); 54.159 (C1'); 44.964 (C1, C5); 26.964 ($CH_2$); 24.293 ($CH_2$); 14.019 (imidazole Me2).

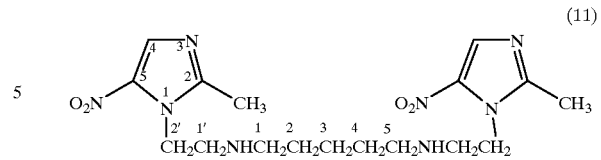

Preparation of N, N'-di[2'-(2-methyl-5-nitro-1-imidazolyl)-1,5-pentane-diamine The above combined aqueous solution was reextracted 3 times with 250 ml of ethyl acetate and 3 times with 500 ml of methylene chloride. The methylene chloride solution was washed with 40 ml of water, dried over MgSO4, and evaporated under reduced pressure. The residual oil was cooled at 4° C. to crystalize. The resulting solid was recrystallized from ethyl acetate/hexane to give N, N'-di[2'(2-methyl-5-nitro-1-imidazolyl)-1,5-pentanediamine.

The chemical structure analysis was performed by $^1H$ NMR ($CDCl_3$, 300 MHz) δ7.93 (s, 2H, imidazole H4); 4.38 (t, J=6.6 $H_z$, 4H, H2'); 2.94 (t, J=6.6 $H_z$, NH, N'H); 1.42–1.22 (m, 6H, H2, H3, H4).

EXAMPLE 4

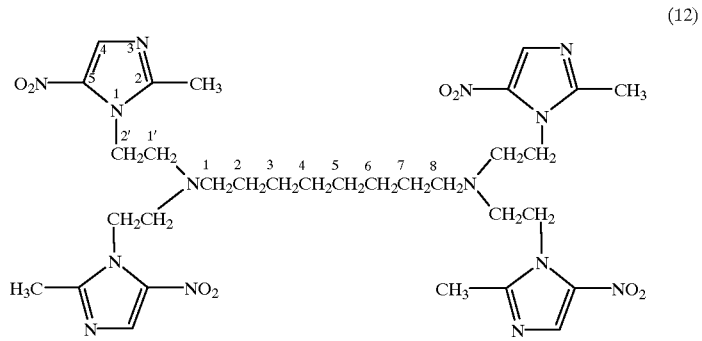

Preparation of N, N, N', N'-tetra[2'(2-methyl-5-nitro-1-imidazolyl)ethyl]-1,8-octanediamine The 2-methyl-5-nitroimidazol-1-yl-acetaldehyde (3.52 g, 19 mmol) synthesized by the procedure described in Example 1 was dissolved in 80 ml of 1, 2-dichloroethane, 0.685 g of octanediamine (4.75 mmol) was added, and the reaction mixture was stirred for 30 min and then acidified with 1.08 ml of acetic acid (19 mmol). Then, 4.83 g of sodium triacetoxyborohydride (22.8 mmol) was added as a reducing agent and the solution was stirred for 48 h at room temperature. During the entire procedure the reaction vessel was gassed with nitrogen. The resulting mixture was diluted with 60 ml of ethyl acetate, and the mixture solution was washed with 85 ml of saturated aqueous $NaHCO_3$ and 30 ml of water. The aqueous solution was combined for further extraction of compound 13. The organic layer was dried over anhydrous $MgSO_4$, and the solvent was evaporated to leave residual oil which solidified at 4° C. for 2 days. The obtained solid was recrystallized from ethyl acetate/hexane to give N, N, N', N'-tetra[2'(2-methyl-5-nitro-1-imidazolyl)ethyl]-1, 8-octanediamine (m.p. 157°–158° C.).

The chemical structure analysis was performed by $^1H$ NMR ($CDCl_3$, 300 MHz) δ7.93 (s, 4H, imidazole H4); 4.26 (t, J=6.9 HZ, 8H, H2'); 2.81 (t, J=6.6Hx, 8H, H1'); 2.54–2.51

(m, 4H, H1, H8); 2.50 (s, 12H, imidazole Me2); 1.27–1.22 (m, 12H, H2, H3, H4, H5, H6, H7). Also, the number of carbon atoms present was evaluated by $^{13}$C NMR (CDCl$_3$, 75 MHz) δ150.548 (imidazole C5); 138.908 (imidazole C2); 133.142 (imidazole C4); 54.759 (C2'); 54.045 (C1"); 44.257 (C1, C8); 29.051 (C2, C7); 26.744 (C3, C4, C5, C6); 13.951 (imidazole Me2).

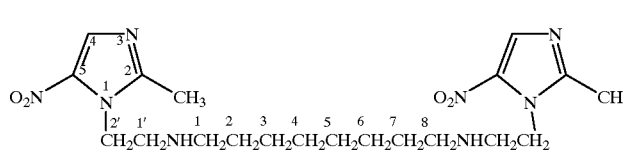

(13)

Preparation of N, N'-di[2'-(2-methyl-5-nitro-1-imidazolyl)-1,8-octanediamine The above combined aqueous solution was reextracted 3 times with 250 ml of ethyl acetate and 3 times with 500 ml of methylene chloride. The methylene chloride solution was washed with 40 ml of water, dried over MgSO$_4$, and evaporated under reduced pressure. The residual oil was cooled at 4° C. to crystallize. The resulting solid was recrystallized from ethyl acetate/hexane to give N, N'-d[2'-(2-methyl-5-nitro-1-imidazolyl)-1,8-octanediamine.

The chemical structure analysis was performed by $^1$H NMR (CDCl$_3$, 300 MHz) δ7.93 (s, 2H, imidazole H4); 4.38 (t, J=6.6 H$_z$, 4H, H2'); 2.94 (t, J=6.6 H$_z$, 4H, H1'); 2.57–2.53 (m, 4H, H1, H8); 2.50 (s, 6H, imidazole Me2); 1.89 (br, s, 2H, NH, N'H); 1.45–1.20 (m, 12H, H2, H3, H4, H5, H6, H7).

EXAMPLE 5

Preparation of N, N, N', N'-tetra[2'-(2-methyl-5-nitro-1-imidazolyl) ethyl]-1,8-octanediamine gluconic acid salt A solution of N, N, N', N'-tetra[2'-(2-methyl-5-nitro-1-imidazolyl)ethyl]-1,8-octanediamine free base was prepared by dissolving 0.5 g of N, N, N', N'-tetra[2'-(2-methyl-5-nitro-1-imidazolyl)ethyl]-1,8-octanediamine in 20 ml of CH$_2$Cl$_2$. To this solution, 2 g of gluconic acid in 5 ml of water was added. To the resultant mixture, pure MeOH was added dropwise until the mixture became a homogeneous solution. To this, 50 ml of ether, followed by 200 ml of hexane were added to precipitate the solid. The reaction mixture was cooled to 4° C., and the precipitated salt was removed by filtration through a sintered glass funnel, washed with anhydrous ether and dried under vacuum. This d-gluconic acid salt is highly soluble in water.

EXAMPLE 6

Preparation of N, N, N', N'-tetra[2'-(2-methyl-5-nitro-1-imidazolyl) ethyl]-,8-octanediamine hydrochloric acid salt N, N, N', N'-tetra[2'-(2-methyl-5-nitro-1-imidazolyl) ethyl]-1,8-octanediamine free base (1 g) is dissolved in 50 ml of warm methanol. To this solution, 5 ml of about 4 N ethanolic hydrochloric acid is added. Ether (20 ml) is then added slowly. The mixture solution is cooled and kept at 4° C. to facilitate precipitation. The precipitate is then collected by suction filtration, and recrystallized with methanol/ether to yield N, N, N', N'-tetra[2'-(2-methyl-5-nitro-1-imidazolyl) ethyl]-1,8-octanediamine.HCl.

EXAMPLE 7

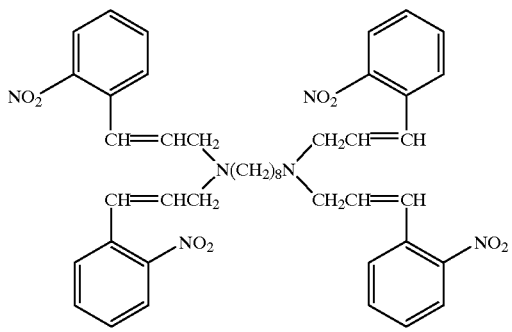

(14)

Preparation of N,N,N',N'-tetra(trans-2-nitrocinnamyl-1,8-octanediamine

Trans-2-nitrocinnamaldehyde (614 mg, 3.17 mmol) was dissolved in 40 ml of 1,2-dichloroethane, 114 mg of octanediamine (0.79 mmol) was added, and the reaction mixture was stirred for 2 hours and then acidified with 0.18 ml of acidic acid (3.17 mmol). Then, 0.81 g of sodium triacetoxyborohydride (3.80 mmol) was added as a reducing agent and the solution was stirred for 48 hours at room temperature. During the entire procedure the reaction vessel was gassed with nitrogen. The resulting mixture was diluted with 30 ml of ethyl acetate, and the mixture solution was washed with 45 ml of saturated aqueous NaHCO$_3$ and 20 ml of water. The ethyl acetate solution was dried over anhydrous MgSO$_4$. The solvent was evaporated to leave residual oil which was purified by chromatography to give N, N, N', N'-tetra(trans-2-nitrocinnamyl)-1, 8-octanediamine.

The chemical structure analysis was performed by $^1$HNMR (CDCl$_3$, 300 MHz) δ7.94–7.90 (m, 4H, phenyl H3); 7.63–7.53 (m, 8H, phenyl H4 and H5); 7.41–7.26 (m, 4H, phenyl H6); 7.09 (d, J=15.9 Hz, 4H, H3'); 6.39–6.29 (m, 4H H2'); 3.48 (d, J=5.7 Hz, 8H, H1'); 2.68 (br s, 4H, H1, H8); 1.61 (br s, 4H, H2, H7); 1.32 (br s, 8H, H3, H4, H5, H6).

EXAMPLE 8

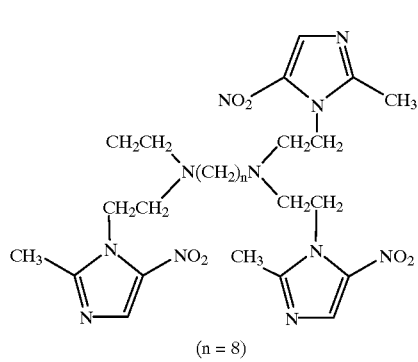

Preparation of N, N, N'-tri[2'-(2-methyl-5-nitro-1-imidazolyl) ethyl]-N'-ethyl-1,8-octanediamine Ten mmole of 1,8 diaminooctane is dissolved in 50 ml of pyridine. Five mmole of $Ac_2O$ is added to the solution dropwise at 10° C. The organic solvent is then evaporated. Using column chromatography, N-monoacetoamide-1,8-diaminooctane subsequently is separated out. The N-monoacetoamide-1,8-diaminooctane is dissolved in 25 ml 1,2-dichloroethane. To this solution, 6 mmole of $LiAlH_4$ is added. The solution is then stirred under nitrogen gas at room temperature for 1 day. Subsequently, the solution is diluted with 100 ml of ethyl acetate. The resulting solution is washed with 20 ml of saturated sodium chloride solution. The solution is dried over $MgSO_4$ and evaporated to produce a residue of N-monoethyl-1,8-diaminooctane. The obtained N-monoethyl-1,8-diaminooctane is dissolved in 80 ml of 1,2-dichloroethane containing about 15 mmole of 2-methyl-5-nitro-imidazolyl-1-yl-acetaldehyde. This reaction mixture is stirred for 30 minutes and then acidified with 15 mmole of acetic acid. Eighteen mmole of sodium triacetoxyborohydride is added as a reducing agent and the solution is stirred for 48 hours at room temperature. The resulting mixture is diluted with 80 ml of ethyl acetate, and the mixture solution is washed with 100 ml of saturated aqueous $NaHCO_3$ and 50 ml of water. The organic layer is dried over anhydrous $MgSO_4$, and the solvent is evaporated to leave residual oil which solidified at 4° C. for 2 days. The obtained solid is recrystallized from ethyl acetate/hexane to give N, N, N'-tri[2'-(2-methyl-5-nitro-1-imidazolyl) ethyl]-N'-ethyl-1,8-octanediamine.

EXAMPLE 9

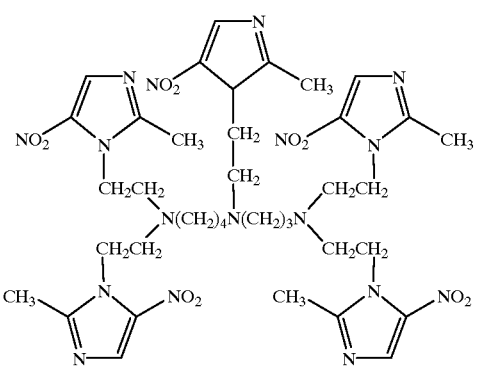

Preparation of N-[2'-(2-methyl-5-nitro-1-imidazolyl) ethyl]-N-{3-N'', N''-di[2'-(2-methyl-5-nitro-1-imidazolyl)ethyl]-aminopropyl}-N', N'-di[2'-(2-methyl-5-nitro-1-imidazolyl]-1,4-butanediamine 2-methyl-5-nitroimidazol-1-yl-acetaldehyde (699 mg, 4.14 mmol), which was synthesized in our laboratory, was dissolved in 40 ml of 1,2-dichloroethane. Subsequently, 120 mg (0.131 ml) of spermidine (0.828 mmol) was added to the solution, and the reaction mixture was stirred for 2 hours, and then acidified with 0.24 ml of acetic acid (4.14 mmol). Then, 1.05 g of sodium triacetoxyborohydride (4.50 mmol) was added and the solution was stirred for 48 hours at room temperature. During the entire procedure the reaction vessel was gassed with nitrogen. The resulting mixture was diluted with 30 ml of ethyl acetate, and the mixture solution was washed with 45 ml of saturated aqueous $NaHCO_3$ and 20 ml of water. The ethyl acetate solution was dried over anhydrous $MgSO_4$. The solvent was evaporated to leave residual oil which was purified by chromatography to give N-[2'-(2-methyl-5-nitro-1-imidazolyl)ethyl]-N-{3-N'', N''-di[2'-(2-methyl-5-nitro-1-imidazolyl)ethyl]-aminopropyl}-N', N'-di[2'-(2-methyl-5-nitro-1-imidazolyl]-1, 4-butanediamine.

The chemical structure analysis was performed by $^1$HNMR ($CDCl_3$, 300 MHz) $\delta$7.89 (s, 5H, imidazole H4), 4.25 (t, J=6.0 Hz, 10H, H2'); 2.78 (t, J=6.6 Hz, 10H, H1'); 2.52–2.49 (m, 8H, H1, H4, H1'', H3''); 2.50 (s, 15H, imidazole Me2); 1.20–1.23 (m, 6H, H2, H3, H2'').

EXAMPLE 10

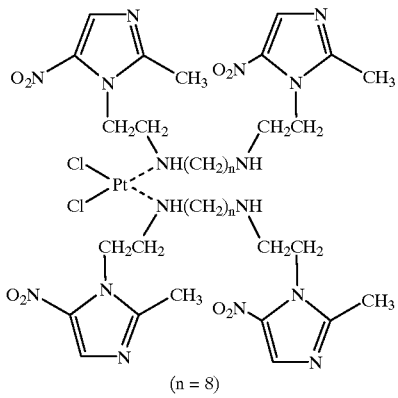

(17)

(n = 8)

Preparation of (DADM)$_2$PtCL$_2$

Cis-bis(acetonitrile)dichloroplatinum (II) (392 mg, 1 mmole) is added to 20 ml of chloroform and stirred until dissolved. Two mmole (896 mg) of 8-carbon DADM (i.e., n is 8) in 10 ml of chloroform is then added to the mixture. The reaction mixture is stirred overnight at room temperature. Subsequently, the temperature of the solution is lowered to 4° C. to cause precipitation of crude (DADM)$_2$PtCl$_2$. The precipitate is collected by suction filtration and then washed with methanol to produce the (DADM)$_2$PtCl$_2$.

EXAMPLE 11

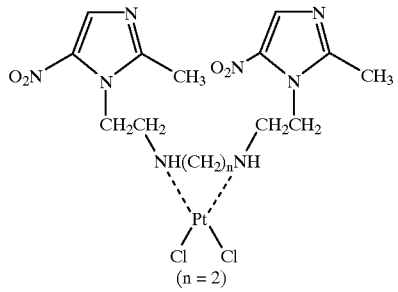

(18)

(n = 2)

Preparation of {N, N'-di[2-(2-methyl-5-nitro-1-imidazolyl)-1,4-ethylenediamine}PtCl$_2$ Cis-bis(acetonitrile)dichloroplatinum (II) (1 mmole) is added to 20 ml of chloroform and stirred until dissolved. One mmole of N, N'-di[2-(2-methyl-5-nitro-1-imidazolyl)-1,4-ethylenediamine in 10 ml of chloroform is then added to the mixture The reaction mixture is stirred overnight at room temperature. Subsequently, the temperature of the solution is lowered to 4° C. to cause precipitation of crude {N, N'-di[2-(2-methyl-5-nitro-1-imidazolyl)-1,4-ethylenediamine}PtCl$_2$. The precipitate is collected by suction filtration and then washed with methanol to produce the {N, N'-di[2-(2-methyl-5-nitro-1-imidazolyl)-1,4-ethylenediamine}PtCl$_2$.

EXAMPLE 12

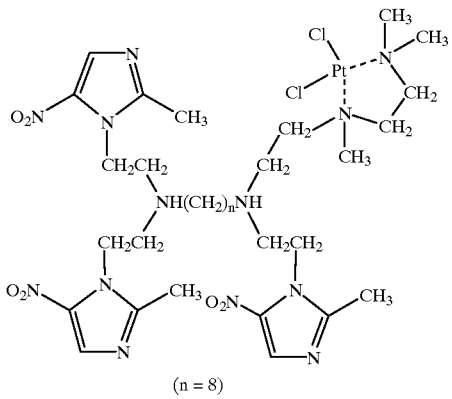

(19)

(n = 8)

Preparation of {N,N,N'-tri[2-methyl-5-nitro-1-imidazolyl)ethyl]-N'-[2'(N,N,N'-trimethyl-ethylenediamine)ethyl]-1,8-octanediamine}PtCl$_2$ 1,8-octanediamine (2.9 g, 20 mmole) is dissolved in 100 ml of 1,2-dichloroethane. N,N,N'-trimethyl-N'-acetaldehyde-ethylenediamine (144 mg, 1 mmole) in 10 ml of chloroform is added dropwise. The reaction mixture is stirred under nitrogen gas at room temperature for 1 hour. Then, 0.06 ml of acetic acid (1 mmole) and sodium triacetoxyborohydride (0.25 g, 1.2 mmole) is added to the reaction solution. The solution is stirred for 2 hours. The resulting solution is diluted with 100 ml of ethyl acetate, and rinsed with 40 ml of saturated aqueous NaHCO$_3$, and 40 ml of saturated aqueous NaCl. The organic solvent layer is dried over MgSO$_4$, and evaporated to leave a residual oil. The crude oil is purified by Al$_2$O$_3$ column chromatography, to yield N-[2'(N,N,N'-trimethyl-ethylenediamine)ethyl]-1,8-octanediamine.

2-methyl-5-nitroimidazol-1-yl-acetaldehyde (1.69 g, 10 mmole), which is synthesized by the procedure described in Example 1, is dissolved in 80 ml of 1,2-dichloroethane. Then, 0.906 g of N-[2'(N,N,N'-trimethyl-ethylenediamine)ethyl]-1,8-octanediamine is added, and the reaction mixture is stirred for 30 min and then acidified with 0.57 ml of acetic acid (10 mmole). Subsequently, 2.54 g of sodium triacetoxyborohydride (12 mmole) is added as a reducing agent and the solution was stirred for 48 h at room temperature. During the entire procedure the reaction vessel is gassed with nitrogen. The resulting mixture is diluted with 60 ml of ethyl acetate, and the mixture solution is washed with 85 ml of saturated aqueous NaHCO$_3$ and 30 ml of water. The aqueous solution is combined for further extraction of compounds containing only one nitroimidazole group. The organic layer is dried over anhydrous MgSO$_4$, and the solvent was evaporated to leave residual oil which solidified at 4° C. for 2 days. The obtained solid is recrystallized from ethyl acetate/hexane to give N,N,N'-tri[2-methyl-5-nitro-1-imidazolyl)ethyl]-N'-[2'(N,N,N'-trimethyl-ethylenediamine)ethyl]-1,8-octanediamine.

To form the metal complex with the nitrogens in the N,N,N'-trimethyl-ethylenediamine)ethyl substituent, the following procedure is used. Cis-bis(acetonitrile) dichloroplatinum (II) (1 mmole) is added to 20 ml of chloroform and stirred until dissolved. One mmole of N,N,N'-tri[2-methyl-5-nitro-1-imidazolyl)ethyl]-N'-[2'(N,N,N'-trimethyl-ethylenediamine)ethyl]-1,8-octanediamine in 10 ml of chloroform is then added to the mixture. The reaction mixture is stirred overnight at room temperature. Subsequently, the temperature of the solution is lowered to 4° C. to cause precipitation of crude {N,N,N'-tri[2-methyl-5-nitro-1-imidazolyl)ethyl]-N'-[2'(N,N,N'-trimethyl-ehtylenediamine)ethyl]-1,8-octanediamine}PtCl$_2$. The precipitate is collected by suction filtration and then washed with ethanol to produce the {N,N,N'-tri[2-methyl-5-nitro-1-imidazolyl)ethyl]-N'-[2'(N,N,N'-trimethyl-ehtylenediamine)ethyl]-1,8-octanediamine}PtCl$_2$.

EXAMPLE 13
Adding Hydrophilic Groups

Hydrophilic groups may be attached to the compounds of this invention to impart water-solubility to the compounds. For example, —(CH$_2$)$_8$NH$_2$ may be attached to a secondary amine of DADM by dissolving 5 mmole of DADM and 5 mmole of 8-aminocaprylic acid in 25 ml of pyridine at room temperature; adding 5 mmole of Ac$_2$O to this solution; and allowing the mixture to sit for 3 days while exposed to the atmosphere at room temperature. During these 3 days, the organic solvent will evaporate, leaving the desired product behind as a residue. Likewise, —CH$_2$CH$_2$CH(SO$_3$H)CO$_2$H, may be attached to a secondary amine of DADM by dissolving 5 mmole of DADM and 5 mmole of sulfosuccinic acid in 25 ml of pyridine at room temperature; adding 5 mmole of Ac$_2$O to this solution; and allowing the mixture to sit for 3 days while exposed to the atmosphere at room temperature. Similarly, —CH$_2$(CHOH)$_4$CH$_2$OH may be attached to a secondary amine of DADM by dissolving 5 mmole of DADM and 5 mmole of gluconic acid in 25 ml of pyridine at room temperature;

adding 5 mmole of Ac$_2$O to this solution; and allowing the mixture to sit for 3 days while exposed to the atmosphere at room temperature.

EXAMPLE 14
Chemotherapeutic Effects on *H. pylori* bacteria

Eight-carbon DATM (i.e., n is 8) was tested in vitro for chemotherapeutic activity against *H. pylori* by the method of agar dilution. *H. pylori* strain obtained from American Tissue Culture Collection (ATCC), ATCC43504, was used in the study. Stock cultures were prepared in Brucella Broth (Difco) with 5% fetal bovine serum (FBS) and were stored at −70° C. in 10% glycerol The agar plate was made of 20 ml of 1.5% Mueller-Hinton agar, 2.8% Brucella Broth, 5% FBS, and 0.5 ml of different drug concentrations. The agar plate was dried before inoculation. Then, 0.1 ml of *H. pylori* suspension yielding approximately 150 colony-forming units (CFU) was added onto each plate. Using a hockey stick, the *H. pylori* bacteria were well spread. Plates were allowed to dry briefly and then were put into a chamber. The chamber was flowed with a gas mixture (5% O$_2$, 10% CO$_2$, and 85% N$_2$) for 12 min. After treatment with the microaerophilic atmosphere, the chamber was closed and incubated at 37° C. in incubator for 2 days. The plates were examined for visible growth. The lowest concentration of drug resulting in complete inhibition of growth was taken as the minimum inhibition concentration (MIC).

Figure 2:
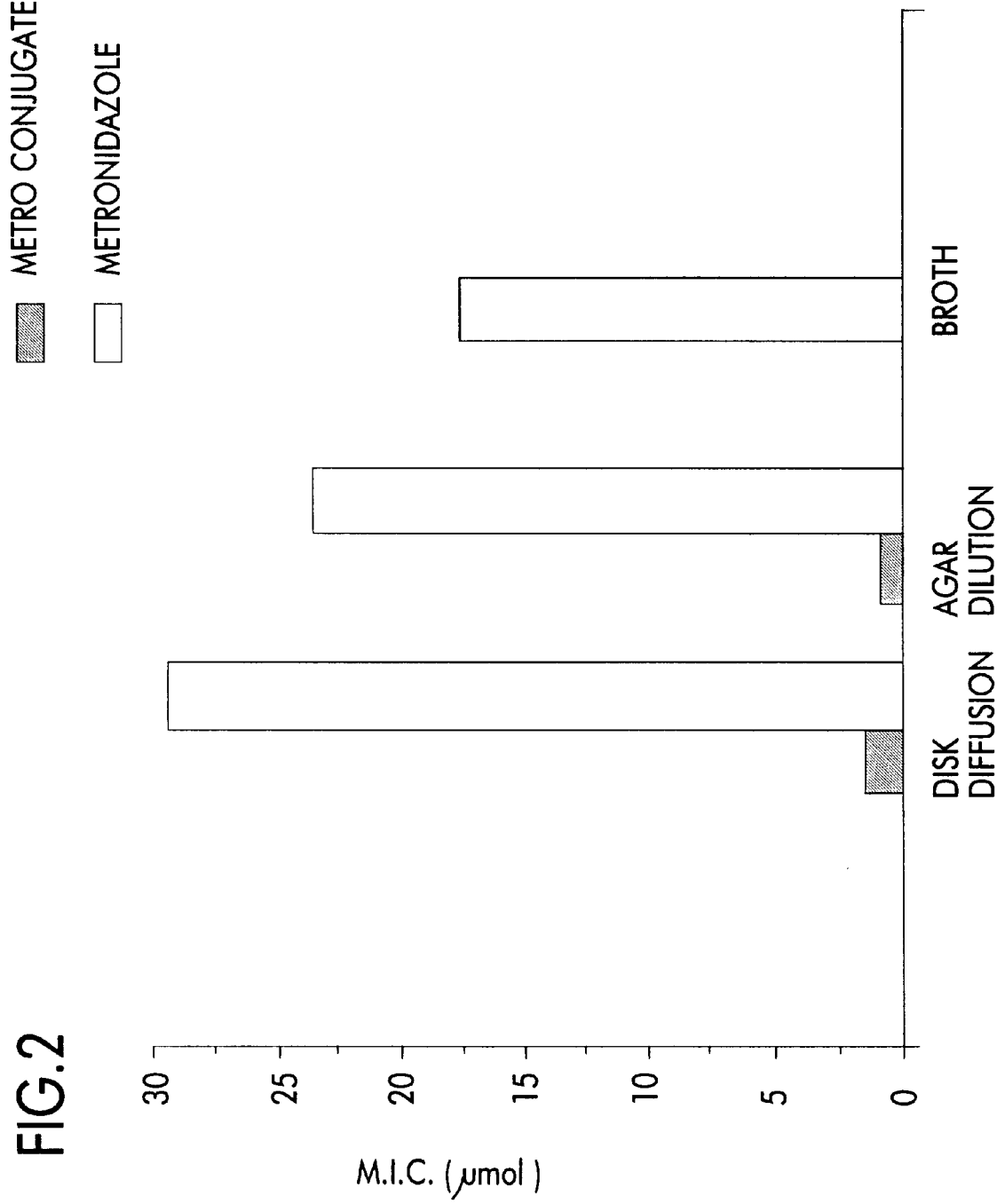
FIG. 2 compares the minimum inhibition concentration ("M.I.C.") of 8-carbon DATM and metronidazole using the disk diffusion method, agar dilution method, and modified bottle broth method.
Figure 3:
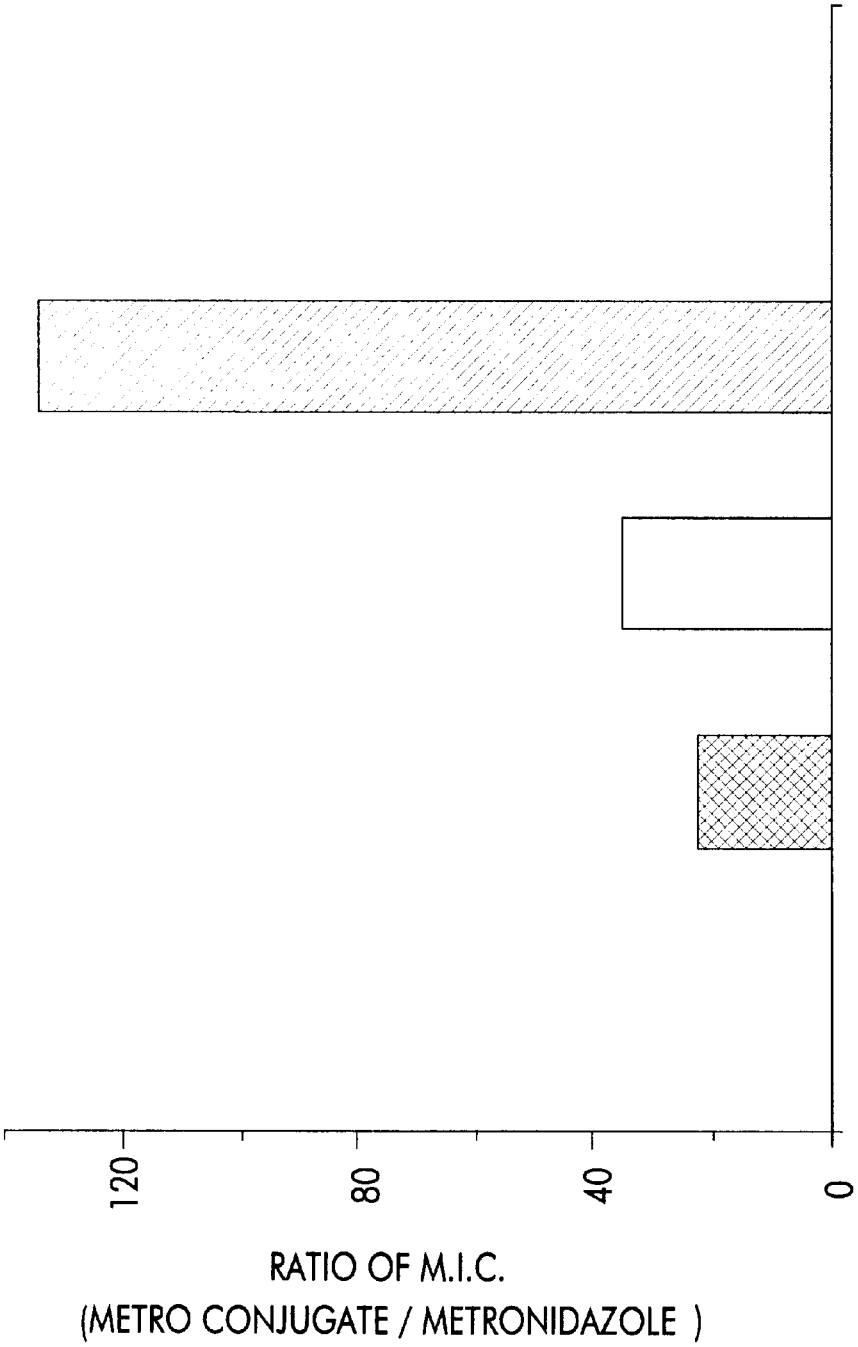
FIG. 3 compares the ratio of M.I.C. (8 carbon DATM/metronidazole) using the disk diffusion method, agar dilution method, and modified bottle broth method.
Figure 4:
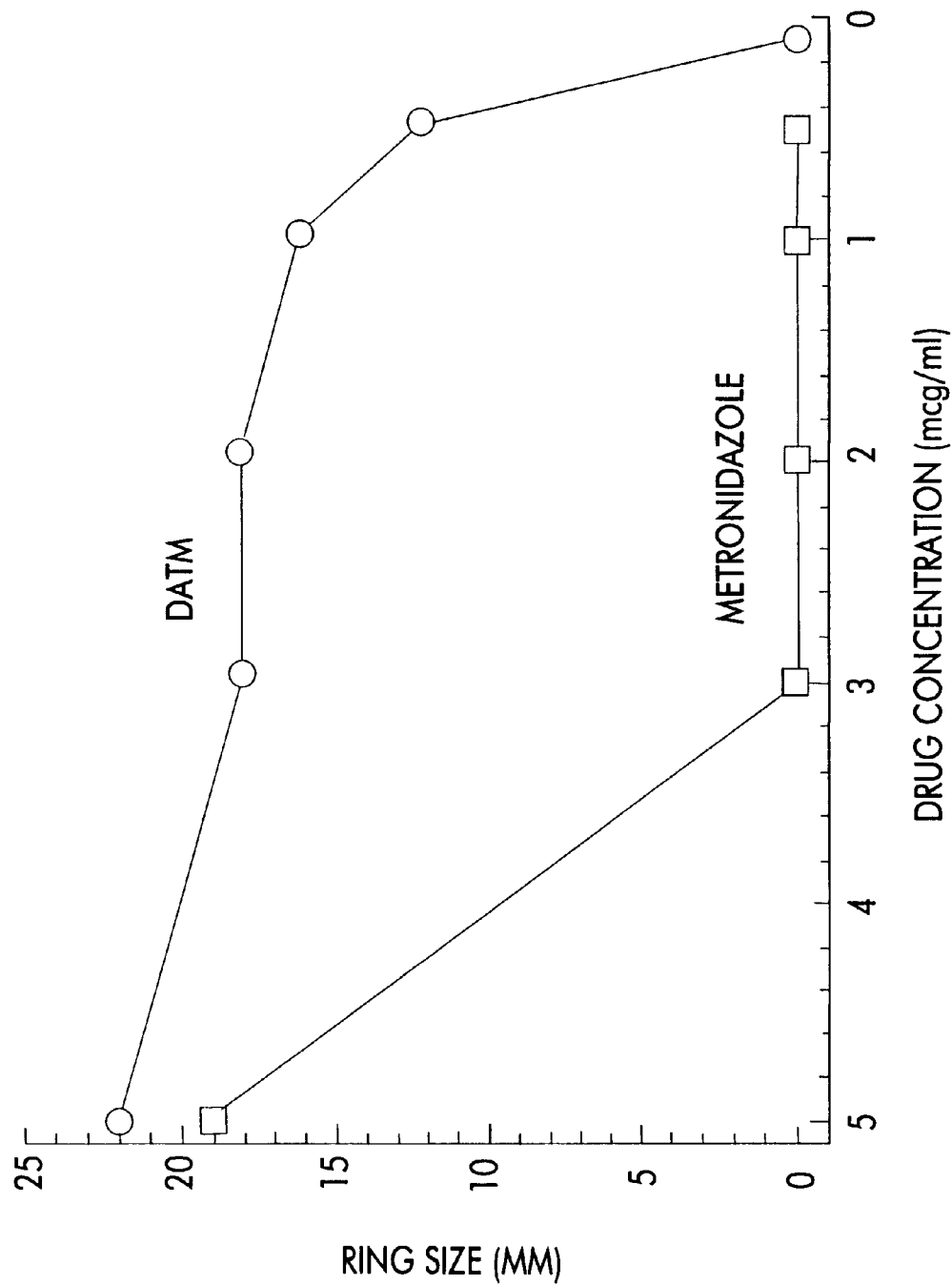
FIG. 4 compares the ring sizes formed at different drug concentrations for 8-carbon DATM and metronidazole.
Figure 5:
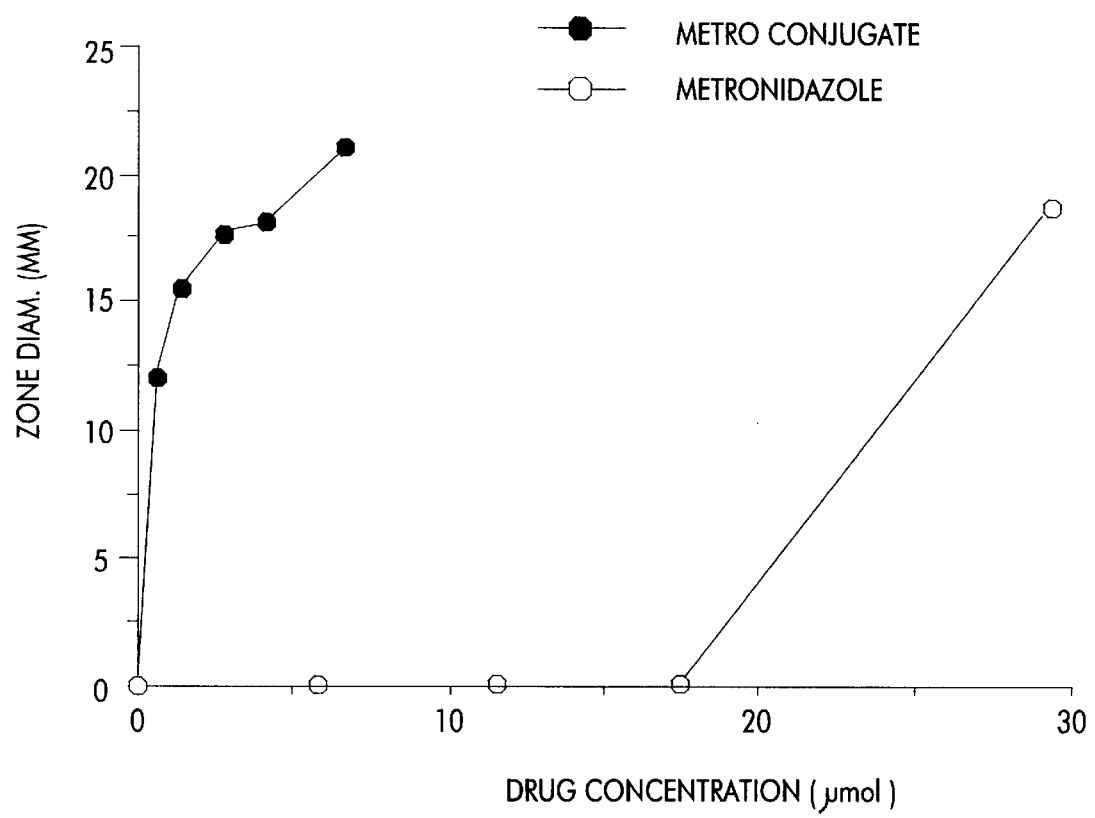
FIG. 5 compares the effects of 8-carbon DATM and metronidazole on *H. Pylori* using the disk diffusion method.

It is known that metronidazole is inhibitory to *H. pylori* growth. In the following experiments, metronidazole was used as parallel comparable agent. FIGS. 1, 2, and 3 show that DATM was extremely more effective in inhibiting *H. pylori* growth than metronidazole. It was found that the MIC values of DATM and metronidazole were 0.66 µmol and 23.39 µmol, respectively. The ratio of the MIC of metronidazole over that of DATM was 35.37. The results were consistent with those obtained by other methods, demonstrating that DATM as significantly more potent than metronidazole in inhibiting the growth of *H. pylori*.

Chemotherapeutic activity of DATM against *H. pylori* was also measured by disk diffusion method. Blood agar plates (Fisher BBL 21239/21261) were used in this experiment. About 1.5×10$^8$ *H. pylori* bacteria in Brucella Broth solution were added onto plates and spread evenly across the agar surface using a hockey stick. The plates were briefly dried, and then 6-mm disks containing drugs were added. The plates were put into a gassing chamber leaving outflow open. The chambers were flowed with a mixture gas (5% O$_2$, 10% CO$_2$, and 85% N$_2$) for 12 min, then closed tightly, and placed in 37° C. incubator for 4 days. The diameter of the zone of the growth inhibition was examined.

As shown in FIGS. 2, 3, 4, and 5 that DATM exhibited remarkably more effectiveness against *H. pylori* than metronidazole. The MIC value (inhibition zone, ≧15 mm diameter) was 1.32 µmol for DATM, and 29.24 µmol for metronidazole. Therefore, DATM was 22.1 times more potent than metronidazole in killing *H. pylori*. These results were reproducible and coincidental with previous data using the agar dilution method.

*H. pylori* bacteria also were tested by a modified bottle broth method. Culture media containing 2.8% Brucella Broth, and 1% resazurin (mg/ml) as oxygen an indicator, were prepared freshly on the day of experiment. Experimental bottles each containing 9.4 ml of media were bubbled with a mixture gas (5% O$_2$, 10% CO$_2$, and 85% N$_2$) for 15 min, and then autoclaved for 20 min. When they cooled to room temperature, 0.1 ml of *H. pylori* suspension and 0.5 ml FBS was added into each bottle containing different drug concentrations. After inoculating the bottles with *H. pylori*, the bottles were placed in a 37° C. shaker water bath for about 2 days. Turbidity in each bottle was used as an indicator of the MIC.

Figure 6:
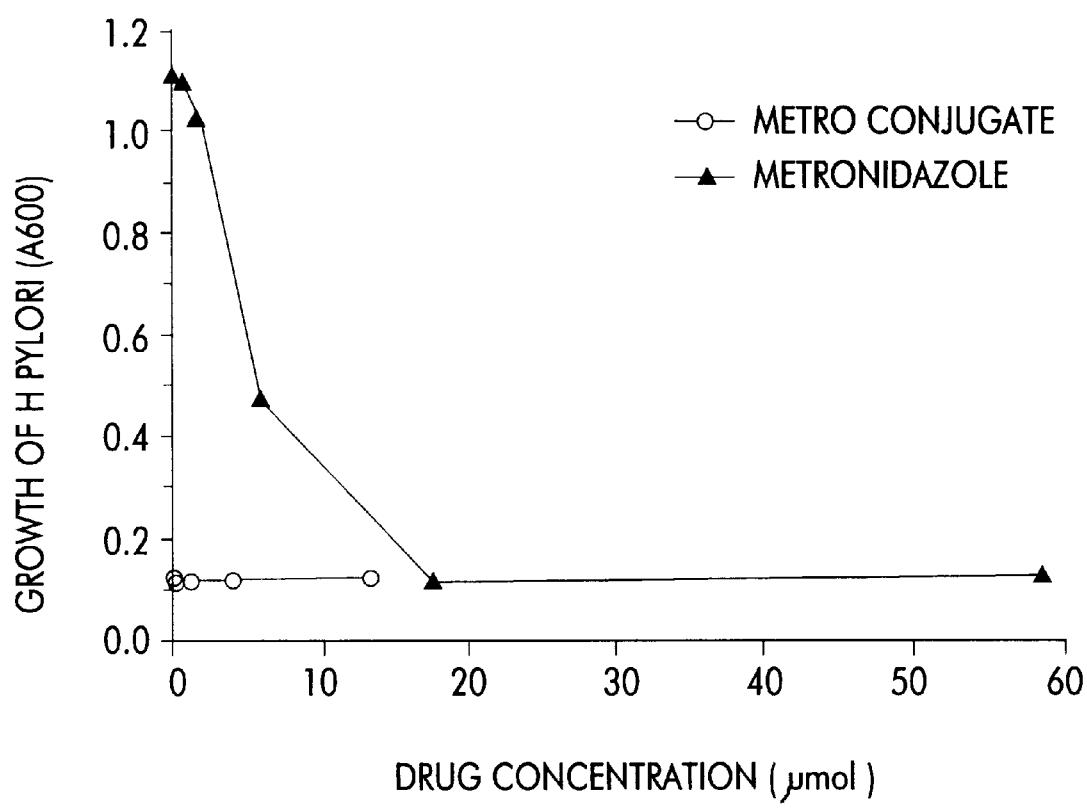
FIG. 6 compares the effects of 8-carbon DATM and metronidazole on *H. pylori* using the modified bottle broth method.

The results in FIGS. 2 and 6 show that DATM was far more effective in inhibiting *H. pylori* growth than metronidazole. The MIC values of DATM and metronidazole were 0.13 µmol and 17.54 µmol, respectively. The ratio of the two MIC (metronidazole/DATM) was 132.63, suggesting that DATM would be greatly better than metronidazole against *H. pylori*. These results along with the data obtained by the other methods demonstrated firmly that DATM is a powerful and potent antibiotic on *H. pylori*.

EXAMPLE 15
Radiosensitization Effects on Hypoxic Tumor Cells

The in vitro radiosensitization effects of compounds (8) and (10) were evaluated on Chinese hamster ovary (CHO) cells, and the results were compared to the effects with metronidazole. Cells were plated and allowed to attach on glass petri dishes for 3 h, then the media was replaced with 5 ml of Hank's balanced salt solution (HBSS) with or without drugs. To induce cell hypoxia, the dishes were placed at room temperature into sealed aluminum chambers (8 dishes/chamber). The chambers were degassed by pumping, and then back-filled with 95% N$_2$ and 5% CO$_2$. This procedure was repeated 4 times with 5 min holding periods under positive gas pressure between evacuations. After 1 h, when the cells were severely hypoxic, the chambers were placed in 37° C. water bath for 1 hr. For oxic treatment groups, cells were placed in 37° C. incubators for 2 h with 5 ml of HBSS (±drugs). The chambers were placed on a rotating table and exposed to an X-ray beam generated by a General Electric Maxitron 300 therapy machine operated at 250 kVp and 20 mA (HVL 20 mm Al filter; dose rate at 2 Gy/min). After irradiation, cells were rinsed with HBSS, and covered with fresh media. Cells were cultured for 7 days in a 37° C. incubator. The resulting cell colonies were stained and counted. The results are shown in Tables 1 and 2.

TABLE 1

Radiosensitization Efficacy of Compounds (8) and (10) on CHO Cells. For Comparison, Values Obtained with Metronidazole are also Shown.

| Compounds | Drug Dose (mM) | SER[a] (N2) | SFR[b] (N2)(18 Gy) | Ratio of RT[c] Dose For 0.04 SF[d] | Do (Gy) |
|---|---|---|---|---|---|
| 8 | 0.1 | .3 | 9.0 | 1.5 | 2.5 |
| 10 | 0.1 | .6 | 21.4 | 1.5 | 1.9 |
| Metronidazole | 0.5 | 1.0 | 1.9 | 1.1 | 3.3 |
| $N_2$ | — | — | — | — | 3.3 |
| $O_2$ | — | — | — | — | 1.4 |

[a] = Sensitizer enhancement ratio is the ratio of the Do for irradiation under hypoxic conditions without the drug divided by the Do with the drug
[b] = Surviving fraction ratio is the ratio of surviving fractions produced by a given radiation dose with and without the drug.
[c] = Radiation therapy
[d] = Surviving fraction

TABLE 2

Radiosensitization Potency of Compounds (8) and (10) on CHO Cells as Compared to Metronidazole

| Compound | Sensitization Ratio at 20% Survival Level |
|---|---|
| 8 | 50 |
| 10 | 400 |

In the experiment shown in Table 2 hypoxic CHO cells were irradiated with a single X ray dose of 8 Gy, with or without drugs. The drug molarity required to reduce cell survival to 20% of the untreated control value was 10 mM for metronidazole, 0.2 mM for compound (8), and 0.025 mM for compound (10). In other words, compound (8) was 50 times and compound (10) was 400 times more potent than metronidazole.

TABLE 3

Radiosensitizing potency of 5 DATM compounds on hypoxic CHO cells as a function of linker length

| Linker Length | Sensitization Ratio at 20% Cell Survival Level |
|---|---|
| 4 | 50 |
| 5 | 80 |
| 6 | 120 |
| 7 | 220 |
| 8 | 510 |

The experiment shown in Table 3 is a later experiment which was conducted to determine the effect of the spacer chain (i.e., A) length. CHO cells were plated and allowed to attach to petri dishes for 3 h, then the media was replaced with 5 ml of Hank's Balanced Salt Solution with or without drugs. To induce cell hypoxia, the dishes were placed in sealed aluminum chambers which were degassed by pumping, and then back filled with 95% $N_2$/5% $CO_2$. After 4 cycles, when the cells were severely hypoxic, the chambers were exposed to an X-ray beam generated by a General Electric Maxitron 300 therapy machine operated at 250 kVp and 20 mA (HVL 20 mm Al filter; dose rate at 2 Gy/min). The cells were cultured for 7 days in a 37° C. incubator and the resulting cell colonies were stained and counted. The cells were subjected to a constant X-ray dose (8 Gy) and various doses of metronidazole (0–10 mM) or DATM (0–0.2 mM). As shown in Table 3, when the spacer chain is 4 carbons long, the DATM is 50 times more potent. And DATM compounds with longer spacer chains were found to be up to about 500 times more effective than metronidazole.

COMBINED DRUG/HEAT EFFECTS

To examine the thermo-radiosensitizing effects of compounds (8) and (10), hypoxic CHO cells were irradiated (with or without drugs) with radiation doses ranging from 0–30 Gy. After irradiation, the chambers were placed either in a 37° C. or in a 41° C. water bath for 30 min. Then cell survival was evaluated by the colony forming assay. The results are presented in Table 4.

TABLE 4

Thermo-radiosensitization Effects of Compounds (8) and (10) on CHO Cells in Presence of Heat (41° C., 30 min)

| Compounds | Drug Dose ($\mu$M) | Do (Gy) |
|---|---|---|
| 8 | 50 | 0.8 |
| 10 | 10 | 0.6 |
| $O_2$ | — | 1.6 |
| $N_2$ | — | 4.0 |

From the results shown in Table 4 it is clear that combining administration of compounds (8) or (10) with mild hyperthermia is even more effective in radiosensitizing CHO cells than treatment with drugs alone. In fact, the magnitude of the combined sensitization effect is such that hypoxic cells become even more radiosensitive (smaller $D_0$) than fully oxic cells.

To determine whether the pronounced effects of DATM in tissue culture can be duplicated in solid tumors, in vivo studies were performed on mice bearing MTG-B mammary adenocarcinoma tumors. The tumors were grown subcutaneously in the right flank of 7-week old female C3H mice. When the tumor diameter reached 8 mm, 8-carbon DATM was administered to groups of mice either intraperitoneally or orally at 2 g/kg, and 2 or 4 h later the tumors were subjected to an X-ray dose of 22 Gy. Control mice bearing identical tumors were either left untreated or treated with radiation alone or drug alone. For irradiation, the mice were placed into lead holders with the tumor-bearing leg exposed. After treatment, the tumor diameters were measured daily by caliper and the time required for tumors to grow to twice their initial size was calculated as tumor doubling time (TDT), with the treatment day defined as Day 0 for all calculations and plots, The survival time for mice was also recorded in all treatment groups.

Figure 7:
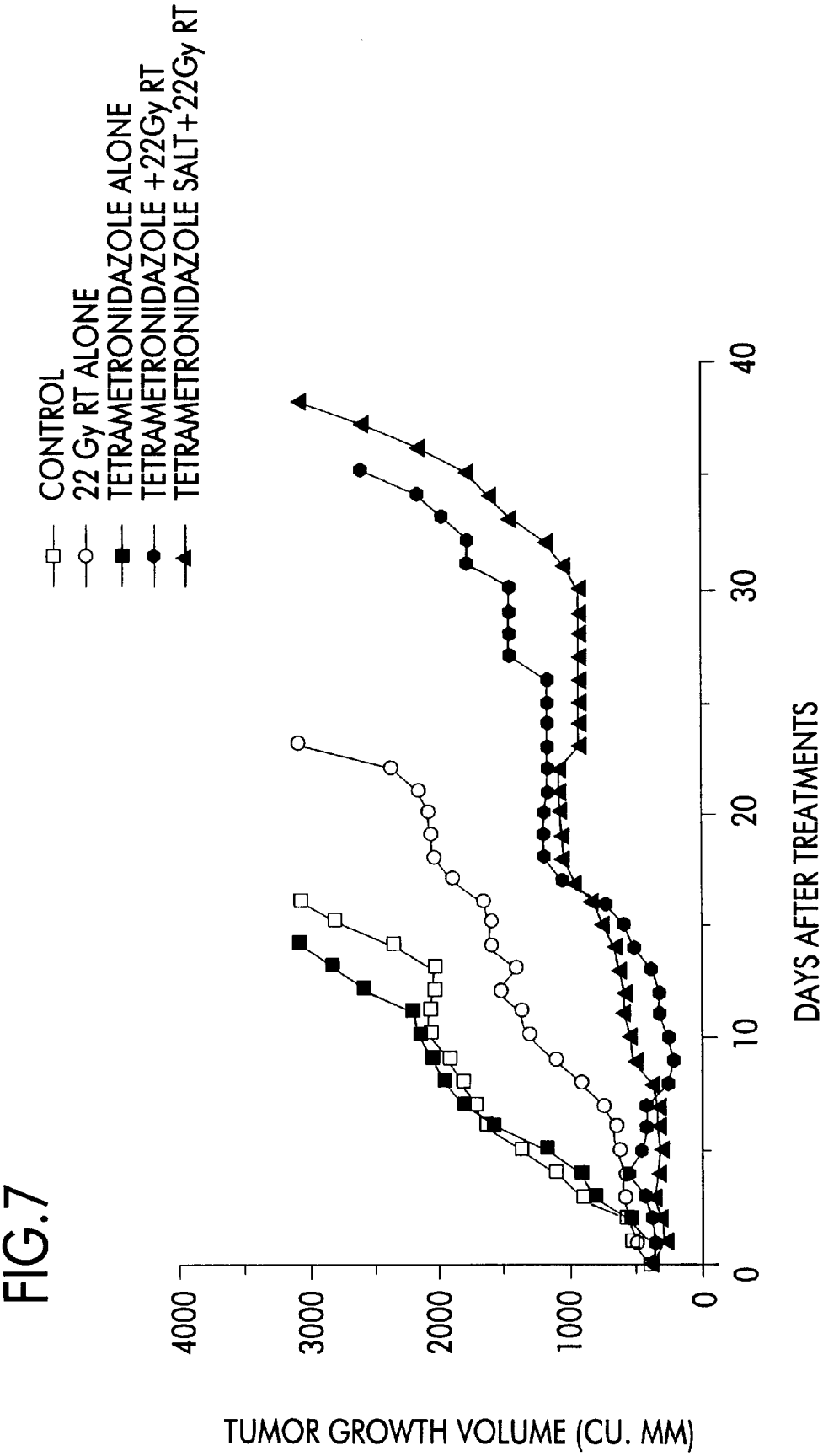
FIG. 7 compares the effect of 8-carbon DATM alone, radiation alone, and 8-carbon DATM+radiation on the growth of MTG-B mammary tumors in mice.

As shown in FIG. 7, tumors in control mice and in mice treated with 8-carbon DATM grew rapidly and the survival time of mice was about 13–15 days. Radiation alone increased the survival time to by an average of 65% to 23 days, but a combination of DATM+radiation increased the survival time by 157–179% to 36 or 39 days In short, DATM+radiation was almost 3 times as effective as radiation alone in delaying tumor growth. The tumor doubling time (TDT) of MTG-B tumors in untreated controls and in mice treated with 8-carbon DATM alone, radiation alone, and DATM+radiation were 3.5, 4, 8.5, and 18 days, respectively. Similar results were obtained in experiments where mice were treated with 5-carbon DATM. These results demonstrate that both DATM compounds are highly effective in radiosensitizing tumors growing in intact animals.

Figure 8:
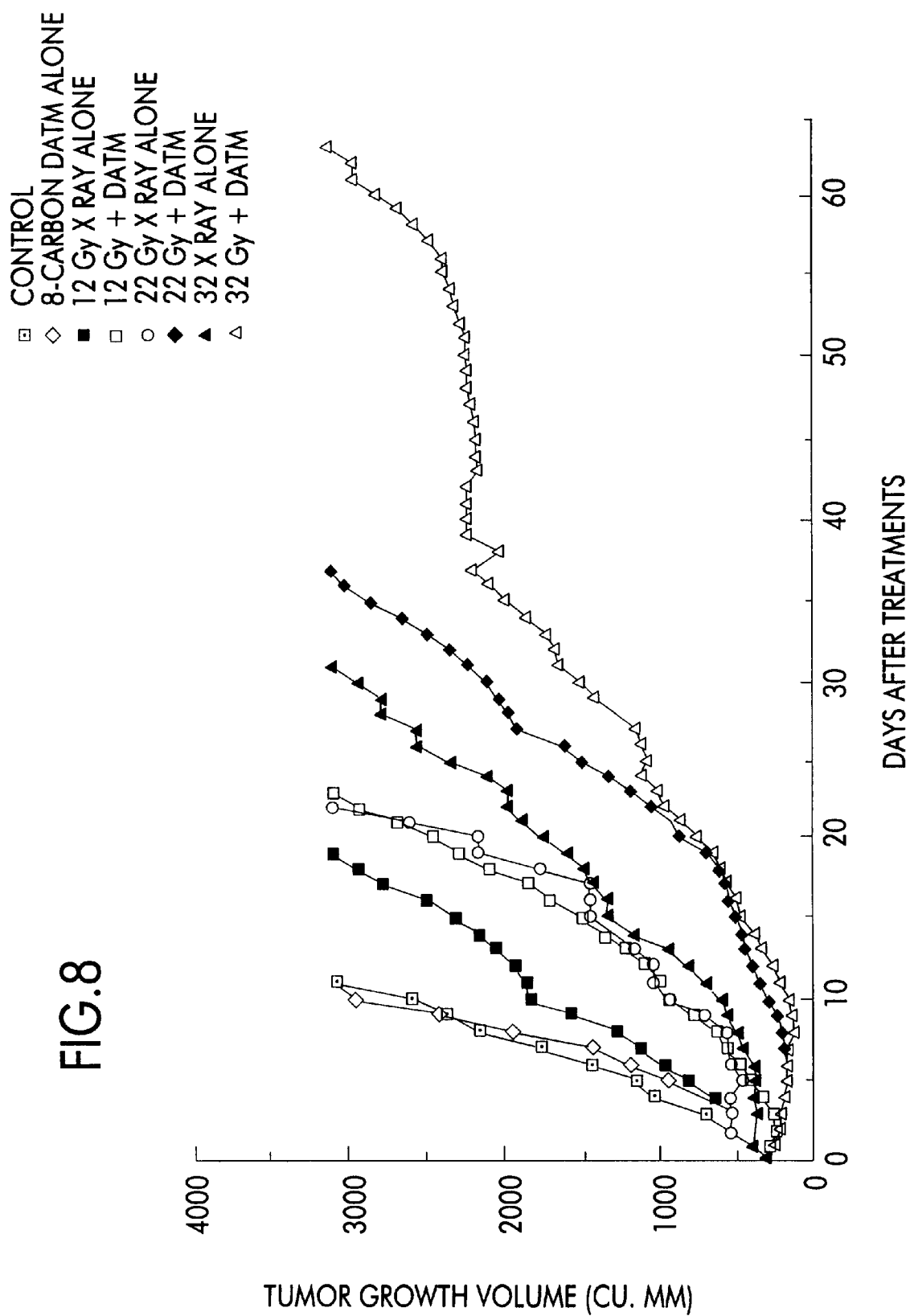
FIG. 8 shows the radiosensitization of MTG-B mammary tumors in mice by 8-carbon DATM (2 g/kg body weight, given orally) as a function of radiation dose (12, 22, and 32 Gy).
Figure 9:
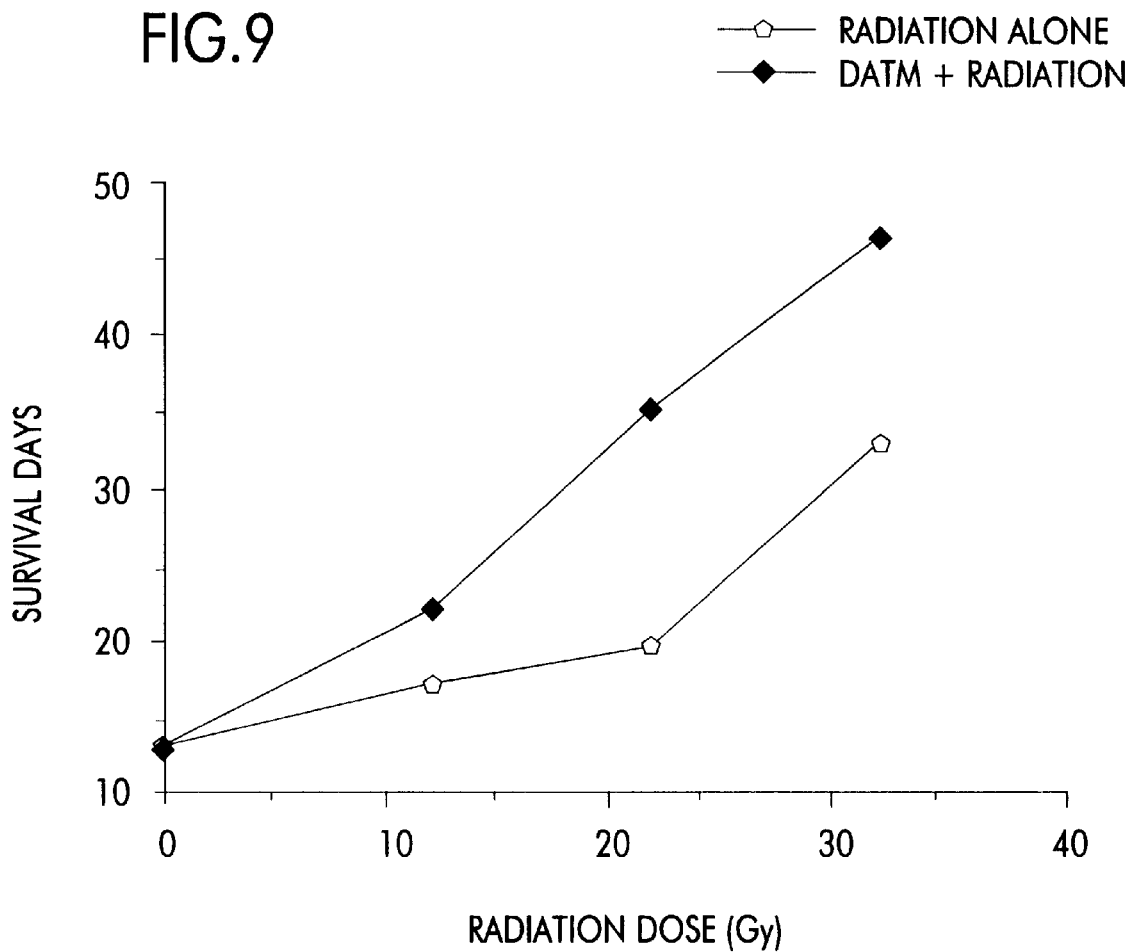
FIG. 9 shows radiosensitization of MTG-B mammary tumors in mice by 8-carbon DATM as a function of radiation dose.

To evaluate radiosensitization at different radiation doses, additional experiments were carried out where mice receiving DATM (2 g/kg body weight, given orally) were exposed to different radiation doses (0, 12, 22, 32 Gy). From the results in FIGS. 8 and 9, it is apparent that DATM causes a pronounced increase in the life span of tumor-bearing mice at all radiation doses studied.

Figure 10:
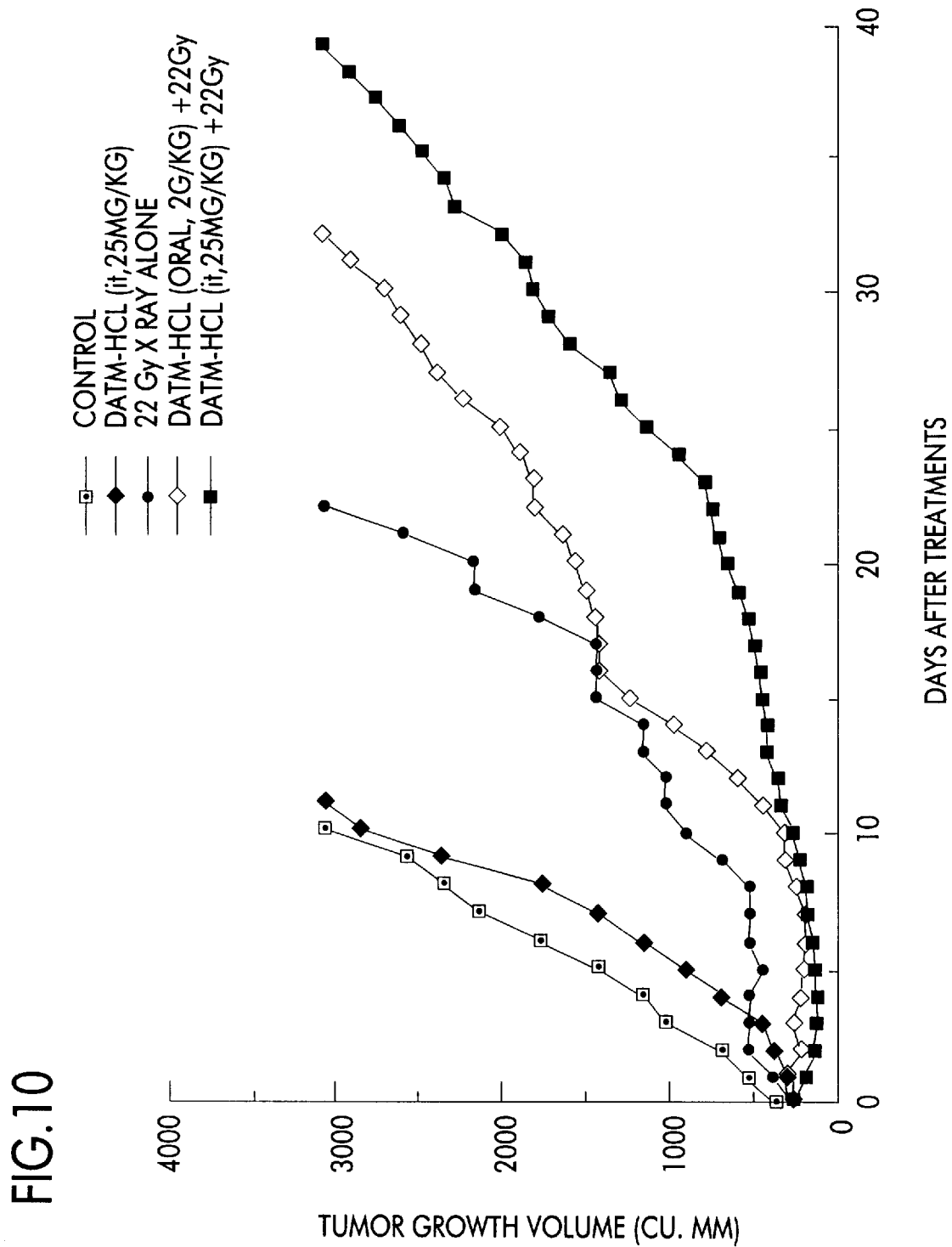
FIG. 10 shows radiosensitization of MTG-B mammary tumors in mice by 8-carbon DATM as a function of the route of drug administration (i.e., oral and intratumor).

FIG. 10 compares the effectiveness of oral DATM (2 g/kg body weight) to that of a much smaller DATM dose (25 mg/kg body weight) injected directly into the tumor.

Figure 11:
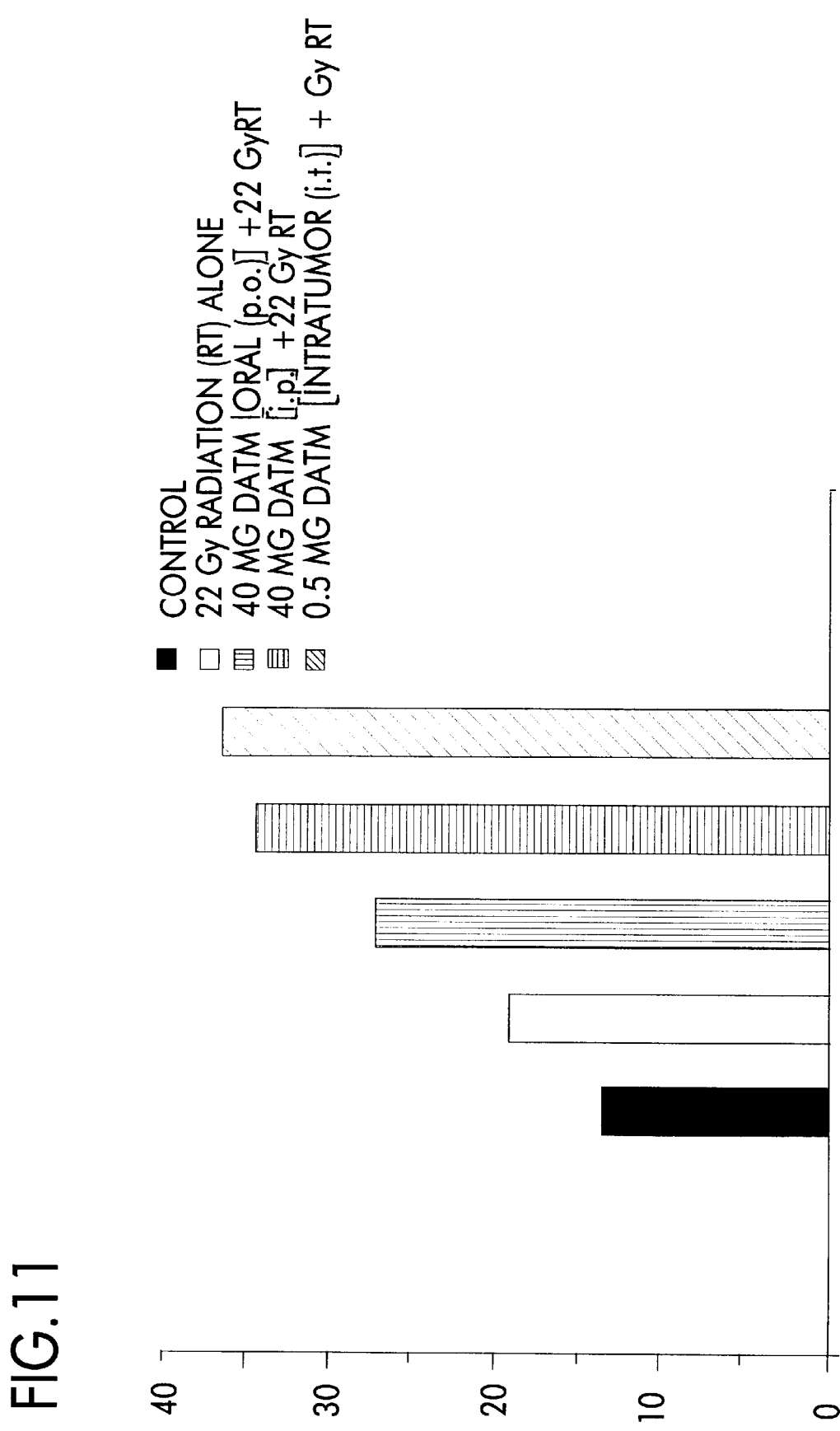
FIG. 11 compares the mean survival of mice with MTG-B tumors as a function of the route of drug administration (i.e., oral, intraperitoneal, and intratumor).

From the results it is obvious that direct intratumor injection of DATM is much more effective than oral drug administration. FIG. 11 summarizes results from several studies where DATM was administered orally, intraperitoneally, or by local intratumor injection. To facilitate a direct comparison, only the 22 Gy radiation day are shown. From the data, it appears that oral DATM is slightly less effective than an equal drug dose administered intraperitoneally. But, by far the most effective route of drug administration is again direct injection into the tumor. Only 25 mg/kg of DATM injected into the tumor produces the same sensitization effect as 2 g/kg given intraperitoneally.

EXAMPLE 16

Toxicity Data (1) In Vitro 0.2 mM DATM (formula 8) and 10 mM metro were administered for 2 hours at 4° C. and found to be equally effective at these dosages in radiosensitizing hypoxic CHO cells. Subsequently, hypoxic CHO cells were incubated with 0.2 mM DATM or 10 mM metro for 12 hours at 37° C. No toxic effects were noted for the CHO cells incubated with the DATM, while the CHO cells incubated with the metro exhibited a 95% reduction in colony formation.

(2) In Vivo

In a preliminary in vivo study, two groups of mice were injected intraperitoneally with either 1 g/kg or 4 g/kg of DATM (formula 8). No toxicity was observed in the 1 g/kg group, but all mice of the 4 g/kg group died. By comparison, the $LD_{50}$ (lethal dose of 50% of animals) for metro is reported to be about 3.3 g/kg. Hence, the toxicity of DATM appears to be roughly comparable to that of metro for the same dosage, yet its radiosensitizing potency is substantially higher.

In a later in vivo study, no toxicity was observed in mice treated orally with 8-carbon DATM doses as high as 20 g/kg, the highest dose that could be force-fed to the animals. In contrast, the $LD_{50}$ (i.e., the lethal dose to 50% of mice) for oral metronidazole was about 4 g/kg. Hence, DATM is at least 5 times less toxic to mice than metronidazole.

In view of the above, it will be seen that the several objects of the invention are achieved and other advantageous results attained.

As various changes could be made in the above compounds and methods without departing from the scope of the invention it is intended that all matter contained in the above description shall be interpreted as illustrative and not in a limiting sense.

We claim:

1. A polyamine compound or a salt thereof, the polyamine compound having the structure:

wherein:
A is a spacer containing a chain having at least 2 atoms in the chain;
$R^1$ is hydrogen, hydrocarbon, heterosubstituted hydrocarbon, heteroaryl, heterosubstituted heteroaryl, or —L—(EAG)$_a$;
$R^2$ is hydrogen, hydrocarbon, heterosubstituted hydrocarbon, heteroaryl heterosubstituted heteroaryl, or —L—(EAG)$_b$;
$R^3$ is hydrogen, hydrocarbon, heterosubstituted hydrocarbon, heteroaryl, heterosubstituted heteroaryl, or —L—(EAG)$_c$;
$R^4$ is hydrogen, hydrocarbon, heterosubstituted hydrocarbon, heteroaryl, heterosubstituted heteroaryl, or —L—(EAG)$_d$;
each L is independently a linker containing a linker chain having at least 1 atom in the chain;
a, b, c, and d are each independently an integer not less than zero, with the sum of a, b, c, and d being no less than 2;
each EAG is independently an electron-affinic group containing (i) a carbocyclic or heterocyclic aromatic moiety which contains a carbonyl, trifluoromethyl, halogen, nitro, nitroso, N-oxide, sulfonyl, sulfinyl, or phosphoryl group; (ii) a heterocyclic aromatic moiety which contains two heteroatoms; (iii) a metal complex; or (iv) an organo-metallic group which contains a metal covalently bonded to carbon; and
the compound or salt contains at least one tertiary amine functionality having three substituents each of which independently contain at least one electron-affinic group or hydrophilic group.

2. The polyamine compound or salt of claim 1 wherein each EAG is independently a heterocyclic aromatic moiety containing two or more heteroatoms.

3. The polyamine compound or salt of claim 1 wherein each EAG is independently selected from the group consisting of imidazoles, triazoles, pyridines, benzamides, nicotinamides, benzotriazine oxides, furans, thiophenes, oxazoles, and thiozoles possessing one or more carbonyl, trifluoromethyl, halogen, sulfonyl, sulfinyl, phosphoryl, nitro, nitroso, or N-oxide groups.

4. The polyamine compound or salt of claim 1 wherein each EAG is independently selected from the group consisting of imidazoles, triazoles, pyridines, benzamides, nicotinamides, benzotriazine oxides, furans, thiophenes, oxazoles, and thiozoles possessing one or more nitro groups.

5. The polyamine compound or salt of claim 1 wherein each EAG is independently a nitro-substituted phenyl group.

6. The polyamine compound or salt of claim 1 wherein at least one EAG is a nitrocinnamyl group.

7. The polyamine compound or salt of claim 1 wherein at least one EAG is selected from the group consisting of quinone and semi-quinone.

8. The polyamine compound or salt of claim 1 wherein the polyamine compound contains a metal complex.

9. The polyamine compound or salt of claim 1 wherein the sum of a, b, c, and d is no less than 3.

10. The polyamine compound or salt of claim 1 wherein the sum of a, b, c, and d is no less than 4.

11. The polyamine compound or salt of claim 1 wherein the sum of a, b, c, and d is no less than 5.

12. The polyamine compound or salt of claim 1 wherein the polyamine compound contains at least one hydrophilic functional group.

13. The polyamine compound or salt of claim 1 wherein the polyamine compound contains one or more functional groups selected from the group consisting of —SO$_3$H, —OH, —NH$_2$, —COOH, —COOR, and —OR and R is hydrocarbon, heterosubstituted hydrocarbon, heteroaryl, or heterosubstituted heteroaryl.

14. The polyamine compound or salt of claim 1 wherein the polyamine compound contains at least one tertiary amine functionality having at least one substituent which contains a hydrophilic functional group.

15. The polyamine compound or salt of claim 1 wherein the polyamine compound contains at least one tertiary amine having at least one substituent which contains one or more functional groups selected from the group consisting of —SO$_3$H, —OH, —NH$_2$, —COOH, —COOR, and —OR and R is hydrocarbon, heterosubstituted hydrocarbon, heteroaryl, or heterosubstituted heteroaryl.

16. The polyamine compound or salt of claim 1 wherein:
A is an unsubstituted hydrocarbon chain having at least 2 carbons in the chain;
each L is independently a linker containing an unsubstituted hydrocarbon chain having at least 1 carbon atom in the chain; and
the sum of a and b is 1 and the sum of c and d is 1.

17. The polyamine compound or salt of claim 16 wherein the polyamine compound contains a tertiary amine functionality having two substituents which each independently contain an electron-affinic group, and a third substituent which contains a hydrophilic group.

18. The polyamine compound or salt of claim 16 wherein the polyamine compound contains a metal complex.

19. The polyamine compound or salt of claim 1 wherein:
three of a, b, c, and d are selected from the set of natural numbers and the other of a, b, c, and d is zero.

20. The polyamine compound or salt of claim 1 wherein:
R$^1$ is -L-EAG;
R$^2$ is -L-EAG;
R$^3$ is -L-EAG;
R$^4$ is -L-EAG; and
each L is independently a linker containing a chain having from 1 to about 20 atoms in the chain.

21. The polyamine compound or salt of claim 20 wherein the polyamine compound contains a metal complex.

22. The polyamine compound or salt of claim 20 wherein the polyamine compound contains at least one hydrophilic functional group.

23. The polyamine compound or salt of claim 20 wherein the polyamine compound contains one or more functional groups selected from the group consisting of —SO$_3$H, —OH, —NH$_2$, —COOH, —COOR, and —OR and R is hydrocarbon, heterosubstituted hydrocarbon, heteroaryl, or heterosubstituted heteroaryl.

24. The polyamine compound or salt of claim 1 wherein:
A is a spacer containing a chain having from 2 to about 30 atoms in the chain;
each L is independently a linker containing a chain having from 1 to about 20 atoms in the chain;

a, b, c, and d are each independently an integer not less than zero; and
the sum of a, b, c, and d is at least 5.

25. A method for making a polyamine having the formula:

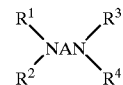

(1)

the method comprising reacting an aldehyde having the formula (EAG)$_n$—A'—CHO with a compound having the formula NH$_2$—A—NH$_2$ in the presence of an organic acid and a reducing agent, wherein A is a spacer containing a chain having at least 2 atoms in the chain;

A' is a linker containing a bond or a chain of at least 1 atom in the chain;

R$^1$ is hydrogen, hydrocarbon, heterosubstituted hydrocarbon, heteroaryl, heterosubstituted heteroaryl, or —L—(EAG)$_a$;

R$^2$ is hydrogen, hydrocarbon, heterosubstituted hydrocarbon, heteroaryl, heterosubstituted heteroaryl, or —L—(EAG)$_b$;

R$^3$ is hydrogen, hydrocarbon, heterosubstituted hydrocarbon, heteroaryl, heterosubstituted heteroaryl, or —L—(EAG)$_c$;

R$^4$ is hydrogen, hydrocarbon, heterosubstituted hydrocarbon, heteroaryl, heterosubstituted heteroaryl, or —L—(EAG)$_d$;

each L is independently a linker containing a linker chain having at least 1 atom in the chain;

a, b, c, and d are each independently an integer not less than zero, with the sum of a, b, c, and d being no less than 2;

n is a natural number;

each EAG is independently an electron-affinic group; and the polyamine contains at least one tertiary amine functionality having three substituents each of which independently contain at least one electron-affinic group or hydrophilic group.

26. The method of claim 25 wherein the reducing agent is NaBH(OAc)$_3$.

27. The method of claim 25 wherein the organic acid is acetic acid.

28. The method of claim 25 wherein the polyamine is selected from the group consisting of spermine, spermidine and triethylenetetramine.

29. The method of claim 25 wherein:
A is a spacer containing a chain having from 2 to about 30 atoms in the chain;
each L is independently a linker containing a linker chain having from 1 to about 20 atoms in the chain; and
the sum of a and b is 1 and the sum of c and d is 1.

30. The method of claim 29 wherein the reducing agent is NaBH(OAc)$_3$.

31. The method of claim 25 wherein A' is a linker containing a bond or a chain having from one to about 19 atoms in the chain.

32. The method of claim 31 wherein the educing agent is NaBH(OAc)$_3$.

33. A method for making a polyamine having the formula:

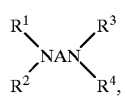
(1)

the method comprising reacting $NH_2ANH_2$ with acetic anhydride to form $CH_3CO\text{—}NHANH_2$, reacting $CH_3CO\text{—}NHANH_2$ with $LiAlH_4$ to form $CH_3CH_2NHANH_2$, and reacting $CH_3CH_2NHANH_2$ with an aldehyde having the formula $(EAG)\text{—}A'\text{—}CHO$ in the presence of an organic acid and a reducing agent, wherein

- A is a spacer comprising a chain having at least 2 atoms in the chain,
- A' is a linker comprising a bond or a chain of from 1 to 19 atoms in the chain,
- $R^1$ is —L—(EAG),
- $R^2$ is —L—(EAG),
- $R^3$ is —L—(EAG),
- $R^4$ is ethyl,
- each L is independently a linker comprising a linker chain having at least 1 atom in the chain, and
- each EAG is independently an electron-affinic group.

34. A method for killing hypoxic tumor cells in a warm-blooded animal, the method comprising:

(a) administering to the warm-blooded animal the compound or salt of claim 1 in an amount effective to radiosensitize the hypoxic tumor cells, (b) followed by, after a time interval sufficient to enhance radiosensitization of the hypoxic tumor cells, irradiating the hypoxic tumor cells with a dose of radiation effective to kill the hypoxic tumor cells.

35. A method for treating a disease in a warm-blooded animal, the method comprising administering to the warm-blooded animal the compound or salt of claim 1.

36. A method for treating a warm-blooded animal having an area which is afflicted by a dermatological disease, the method comprising applying to the afflicted area the compound or salt of claim 1.

37. A composition containing an aldehyde of the formula:

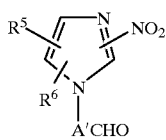
(6)

wherein $R^5$ is hydrogen, lower alkyl or halo;

$R^6$ is hydrogen, lower alkyl, halo or nitro;

A' is a linker comprising a bond or a chain containing at least 1 carbon atom; and the weight ratio of the aldehyde to other compounds in the composition which have as functionality thereof the radical:

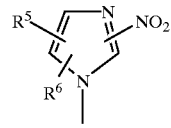

is at least about 1:1.

38. The composition of claim 37 wherein the weight ratio of the aldehyde to said other compounds is at least about 1.8:1.

39. A method for making an aldehyde, the method comprising converting a compound of formula:

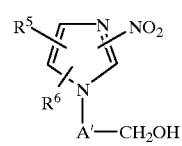
(5)

to a compound of formula:

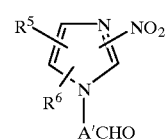
(6)

in a reaction using dimethyl sulfoxide activated by oxalyl chloride, wherein A' comprises a bond or a carbon chain having from 1 to about 19 carbons in the chain, $R^5$ is hydrogen, lower alkyl, or halo, and $R^6$ is hydrogen, lower alkyl, halo, or nitro.

40. The method of claim 39 wherein the compound of formula (5) is dissolved in dimethyl sulfoxide.

41. The composition of claim 37 wherein the weight ratio of the aldehyde to said other compounds is at least about 9:1.

42. A method for making a polyamine having the formula:

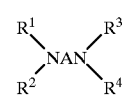
(1)

the method comprising reacting an aldehyde having the formula $(EAG)_n\text{—}A'\text{—}CHO$ with an amine compound in the presence of an organic acid and a reducing agent, wherein:

A is a spacer containing a chain having at least 2 atoms in the chain;

A' is a linker containing a bond or a chain of at least 1 atom in the chain;

$R^1$ is hydrogen, hydrocarbon, heterosubstituted hydrocarbon, heteroaryl, heterosubstituted heteroaryl, or —L—$(EAG)_a$;

$R^2$ is hydrogen, hydrocarbon, heterosubstituted hydrocarbon, heteroaryl, heterosubstituted heteroaryl, or —L—$(EAG)_b$;

$R^3$ is hydrogen, hydrocarbon, heterosubstituted hydrocarbon, heteroaryl, heterosubstituted heteroaryl, or —L—$(EAG)_c$;

$R^4$ is hydrogen, hydrocarbon, heterosubstituted hydrocarbon, heteroaryl, heterosubstituted heteroaryl, or —L—$(EAG)_d$;

each L is independently a linker containing a linker chain having at least 1 atom in the chain;

a, b, c, and d are each independently an integer not less than zero, with the sum of a, b, c, and d being no less than 2;

n is a natural number;

each EAG is independently an electron-affinic group;

the amine compound has at least one primary amine functionality which is bound only to saturated atoms; and the polyamine contains at least one tertiary amine functionality having three substituents each of which independently contain at least one electron-affinic group or hydrophilic group.

43. A method for making a polyamine having the formula:

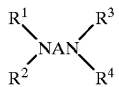

(1)

the method comprising reacting an aldehyde having the formula $(EAG)_n$—A'—CHO with an amine compound in the presence of an organic acid and a reducing agent, wherein:

A is a spacer containing a chain having at least 2 atoms in the chain;

A' is a linker containing a bond or a chain of at least 1 atom in the chain;

$R^1$ is hydrogen, hydrocarbon, heterosubstituted hydrocarbon, heteroaryl, heterosubstituted heteroaryl, or —L—$(EAG)_a$;

$R^2$ is hydrogen, hydrocarbon, heterosubstituted hydrocarbon, heteroaryl, heterosubstituted heteroaryl, or —L—$(EAG)_b$;

$R^3$ is hydrogen, hydrocarbon, heterosubstituted hydrocarbon, heteroaryl, heterosubstituted heteroaryl, or —L—$(EAG)_c$;

$R^4$ is hydrogen, hydrocarbon, heterosubstituted hydrocarbon, heteroaryl, heterosubstituted heteroaryl, or —L—$(EAG)_d$;

each L is independently a linker containing a linker chain having at least 1 atom in the chain;

a, b, c, and d are each independently an integer not less than zero, with the sum of a, b, c, and d being no less than 2;

n is a natural number;

each EAG is independently an electron-affinic group;

the amine compound has at least two amine functionalities, each amine functionality being bound only to saturated atoms and independently being either a primary amine functionality or a secondary amine functionality; and the polyamine contains at least one tertiary amine functionality having three substituents each of which independently contain at least one electron-affinic group or hydrophilic group.

* * * * *